(12) United States Patent
Snellenburg et al.

(10) Patent No.: US 12,711,638 B2
(45) Date of Patent: Aug. 18, 2026

(54) OPHTHMALOGIC SURGICAL SYSTEM

(71) Applicant: Cassini Technologies, B.V., The Hague (NL)

(72) Inventors: Joris-Joost Snellenburg, Delft (NL); Masmei Ginting, Delft (NL); Maarten Huijbregtse, Delft (NL); Benhur Ortiz Jaramillo, Voorburg (NL); Ernst Serfontein, De Hoef (NL); Mark Marie, Richland, MI (US); Joris Vogels, Gemonde (NL)

(73) Assignee: Cassini Technologies, B.V., The Hague (NL)

( * ) Notice: Subject to any disclaimer, the term of this patent is extended or adjusted under 35 U.S.C. 154(b) by 246 days.

(21) Appl. No.: 18/654,978

(22) Filed: May 3, 2024

(65) Prior Publication Data

US 2024/0371010 A1 Nov. 7, 2024

Related U.S. Application Data

(60) Provisional application No. 63/464,015, filed on May 4, 2023.

(51) Int. Cl.
*G06K 9/00* (2022.01)
*A61B 34/10* (2016.01)
(Continued)

(52) U.S. Cl.
CPC .............. *G06T 7/248* (2017.01); *A61B 34/10* (2016.02); *A61B 34/20* (2016.02); *A61B 90/20* (2016.02);
(Continued)

(58) Field of Classification Search
CPC ........... G06T 2207/30041; G06T 7/248; G06T 7/337; G06T 7/74; G06T 2207/10016;
(Continued)

(56) References Cited

U.S. PATENT DOCUMENTS 11,051,884 B2 * 7/2021 Tripathi ............... A61B 3/0025
2009/0048608 A1 2/2009 Boukhny et al.
(Continued)

OTHER PUBLICATIONS

Panagiotopoulou, Eirini-Kanella, et al. “Image-guided lens extraction surgery: a systematic review.” International Journal of Ophthalmology 12.1 (2019): 135. (Year: 2019).*
(Continued)

*Primary Examiner* — Gregory A Morse
*Assistant Examiner* — Owais I Memon
(74) *Attorney, Agent, or Firm* — Womble Bond Dickinson (US) LLP

(57) ABSTRACT

A ophthalmologic surgical system configured to enable scanning and imaging of the anatomical and physiological characteristics of the patient’s eye via the image processing subsystem; to provide for the production of a surgical plan based on imaging and eye data received from the image processing subsystem; and to provide for accurate surgical guidance that is based on the surgical plans produced by the planning subsystem where such surgical guidance is timely corrected and/or adapted to adjust for movement of the patient’s eye in the course of the surgical procedure.

35 Claims, 22 Drawing Sheets

(51) Int. Cl.

| | |
|---|---|
| ***A61B 34/20*** | (2016.01) |
| ***A61B 90/20*** | (2016.01) |
| ***G06T 7/246*** | (2017.01) |
| ***G06T 7/33*** | (2017.01) |
| ***G06T 7/73*** | (2017.01) |
| ***G16H 20/40*** | (2018.01) |

(52) U.S. Cl.
CPC ................ *G06T 7/337* (2017.01); *G06T 7/74* (2017.01); *G16H 20/40* (2018.01); *A61B 2034/2065* (2016.02); *G06T 2207/10016* (2013.01); *G06T 2207/10024* (2013.01); *G06T 2207/10056* (2013.01); *G06T 2207/20081* (2013.01); *G06T 2207/30041* (2013.01)

(58) Field of Classification Search
CPC . G06T 2207/10024; G06T 2207/10056; G06T 2207/20081; A61B 3/0025; A61B 3/13; A61B 34/10; A61B 34/20; A61B 90/20; A61B 2034/2065; A61B 90/361; A61B 2034/258; G16H 20/40; G16H 15/00; G16H 20/30; G16H 30/20; G16H 30/40; G16H 40/67
See application file for complete search history.

(56) References Cited

U.S. PATENT DOCUMENTS

| | | | | |
|---|---|---|---|---|
| 2011/0122365 | A1 | 5/2011 | Kraus et al. | |
| 2011/0230751 | A1* | 9/2011 | Kersting | A61B 3/0025 600/407 |
| 2014/0039510 | A1 | 2/2014 | van Saarloos et al. | |
| 2016/0346047 | A1* | 12/2016 | Tripathi | A61B 34/10 |
| 2021/0307863 | A1* | 10/2021 | Ben-Yishai | G06V 10/443 |
| 2024/0394879 | A1* | 11/2024 | Garbey | G06T 7/246 |

OTHER PUBLICATIONS

Notification of Transmittal and the International Search Report and Written Opinion of the International Search Authority for PCT/IB2024/000266 dated Oct. 8, 2024.

* cited by examiner

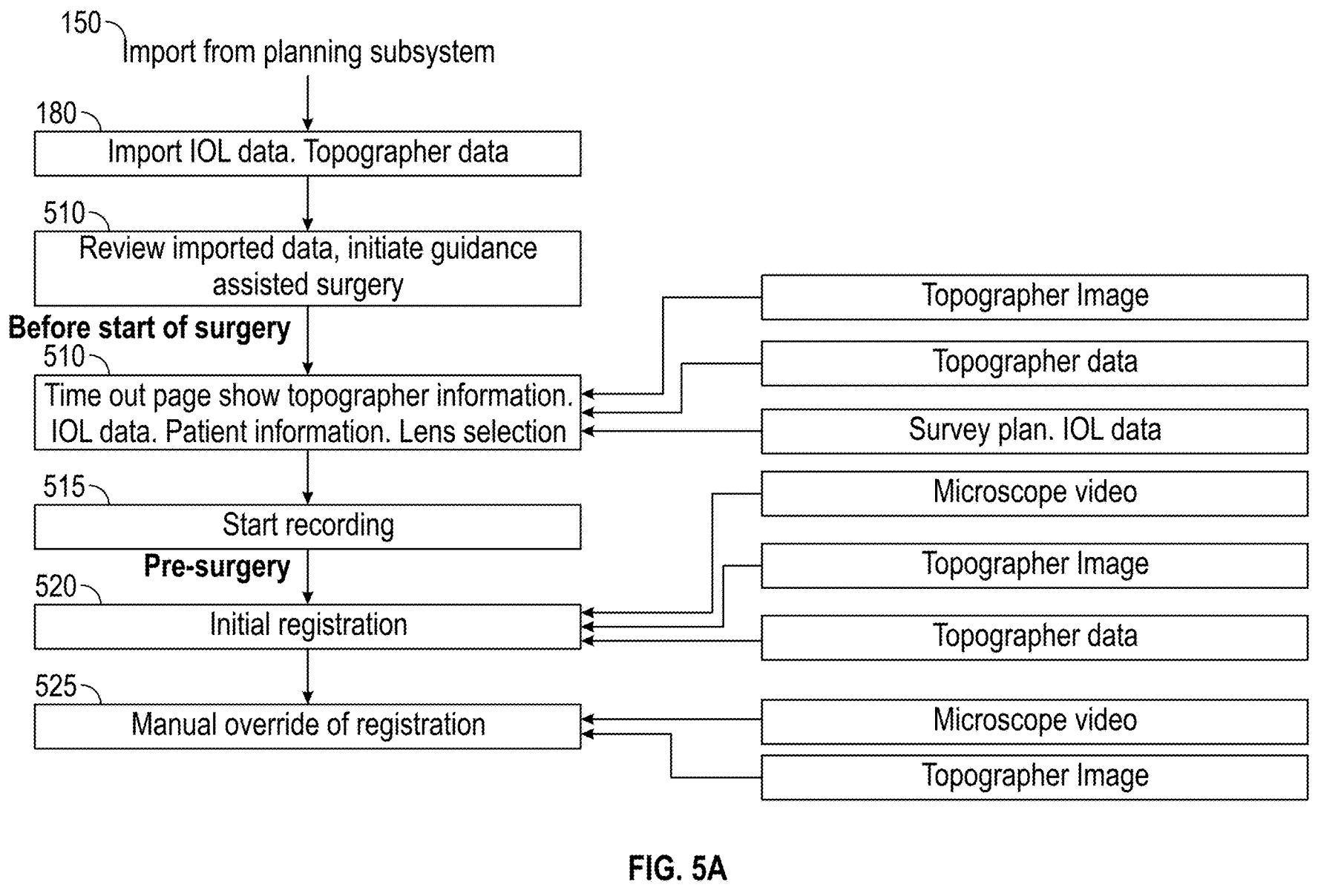

150 Import from planning subsystem

180 Import IOL data. Topographer data

510 Review imported data, initiate guidance assisted surgery

Before start of surgery

510 Time out page show topographer information. IOL data. Patient information. Lens selection 515 Start recording Pre-surgery 520 Initial registration 525 Manual override of registration Topographer Image Topographer data Survey plan. IOL data Microscope video Topographer Image Topographer data Microscope video Topographer Image

FIG. 5A

OPHTHMALOGIC SURGICAL SYSTEM

CROSS-REFERENCE

The present application claims benefit of U.S. Provisional Patent Application No. 63/464,015, filed May 4, 2023.

INCORPORATED BY REFERENCE

The disclosure of U.S. Provisional Patent Application No. 63/464,015, filed May 4, 2023 is specifically incorporated by reference herein as if set forth in its entirety.

TECHNICAL FIELD

The present disclosure relates generally to systems, apparatus and methods in the field of ophthalmic surgery, more particularly, to various aspects involving systems and methods for an improved ophthalmologic surgical system that is configurable for communication with a surgical microscope.

BACKGROUND

In ophthalmology, eye surgery, or ophthalmic surgery, saves and improves the vision of tens of thousands of patients every year. However, given the sensitivity of vision to even small changes in the eye and the minute and delicate nature of many eye structures, ophthalmic surgery is difficult to perform and the reduction of even minor or uncommon surgical errors or modest improvements in accuracy of surgical techniques can make an enormous difference in the patient's vision after the surgery.

Currently, computing systems for assisted ophthalmic surgeries exist (e.g., image guided ophthalmic surgical systems), which include displays that can allow persons (e.g., medical professionals, surgeons, nurses, and/or other persons) to view medical data while a medical procedure is performed. In some systems, a desired location for an object with respect to the ophthalmic surgery can be displayed to a surgeon and, optionally, an object image can be superimposed on (e.g., overlaid with) an intraoperative video stream.

For example, during intraocular lens (IOL) placement procedures, some types of IOLs can require that the IOL is positioned in a specific orientation and/or location within a patient's eye (e.g., Toric IOLs, multifocal IOLs). In current ophthalmic surgery systems, a desired orientation and/or location for the IOL with respect to a preoperative image of an eye (e.g., an image of an eye taken prior to the surgery) can be determined by, for example, various current diagnostic devices. The preoperative image can be captured by the diagnostic device concurrently with sampling the data that is used for calculating the desired IOL positioning (orientation and/or location).

Typically, the position/condition of an eye during preoperative imaging is at least slightly different form the position/condition of the same eye during the ophthalmic surgery. For example, a patient may be sitting when the pre-operative image is taken versus lying down during the ophthalmic surgery. In another example, the eye may have drops and/or tools inserted during the surgery that are not present during the preoperative imaging. Differences in the position/condition of the eye at the time preoperative imaging is done versus the time ophthalmic surgery is performed can result in differences between information in the imaging obtained in a preoperative imaging stage and information obtained during imaging during the ophthalmic surgery (e.g., the intraoperative imaging).

Some current systems can generate a list of feature pairs, one in each of the preoperative image and the intraoperative image, that are assumed to be identical, and use these feature pairs to calculate a global mapping from preoperative image to the intraoperative image. However, there can be distortions in the images due to, for example, liquid inserted into the eye and on the eye, tubes in the eye, tools touching the eye, differences between imaging systems for the pre-operative image and the real-time image, which can cause a best fit to be erroneous.

While current systems may account for some difficulties during surgery, accuracy of the information presented, ease of use of the information presented, and/or timing of the information presented can be improved. Therefore, in view of the prior art, there remains a need for an ophthalmologic surgical system that improves electronically assisted ophthalmic surgical systems.

SUMMARY

To improve the state of the art, disclosed herein is an ophthalmologic surgical system, and methods of use thereof, utilizing novel functionalities. The ophthalmologic surgical system is configured to be operably coupled to a surgical microscope for performance of selected ophthalmologic surgical procedures on the eyes of a patient. The ophthalmologic surgical system includes an image processing subsystem, a planning subsystem, and a surgical guidance subsystem.

It is contemplated that the ophthalmologic surgical system can be configured to enable scanning and imaging of the anatomical and physiological characteristics of the patient's eye via the image processing subsystem; to provide, in the planning subsystem, for the production of a surgical plan based on imaging and eye data received from the image processing subsystem; and to provide, in a surgical guidance subsystem, for accurate surgical guidance that is based on the surgical plans produced by the planning subsystem where such surgical guidance is timely corrected and/or adapted to adjust for movement of the patient's eye in the course of the surgical procedure.

In embodiments, the image processing subsystem can be configured to enable scanning and imaging of the anatomical and physiological characteristics of the patient's eye, which can include, for example, without limitation, color imaging of the patient's eye and topographic measurements of the patient's eye including anterior and posterior surfaces of the cornea and the lens and lens capsule.

In embodiments, the planning subsystem can be configured to generate treatment and surgical guidance planning and can selectively receive imaging data from the image processing subsystem, such as, for example, a full color image of the patient's eye, and topographic eye data to characterize the anatomical and physiological characteristics of the patient's eye. Based on the received topographic eye information and the eye image, the planning system is configured to generate surgical plans and to verify desired eye orientation and planned surgical incisions prior to initiation of a guided surgical procedure on the patient's eye. It is further contemplated that the planning subsystem can include automated plan suggestion using machine learning, learning from a combination of case data and surgeon preference, and/or potentially reducing planning time.

In embodiments, the surgical guidance subsystem can be configured to provide at least one of: patient verification, treatment surgical plan verification, registration of a real-time video image of the patient's eye as displayed to the surgeon via the surgical microscope to the image of the patient's eye that was provided to the surgical guidance subsystem by the planning subsystem; provision of surgical guidance imaging in a visual overlay throughout the surgical procedure in accord with the selected, planned surgical procedure; and tracking identified features on the patient's eye after eye registration to ensure accurate registration of the provided surgical guidance relative to the patient's eye irrespective to movement of the patient's eye throughout the surgical procedure.

Still other aspects, embodiments, and advantages of these exemplary aspects and embodiments, are discussed in detail below. Moreover, it is to be understood that both the foregoing information and the following detailed description are merely illustrative examples of various aspects and embodiments and are intended to provide an overview or framework for understanding the nature and character of the claimed aspects and embodiments. Accordingly, these and other objects, along with advantages and features of the present invention herein disclosed, will become apparent through reference to the following description and the accompanying drawings. Furthermore, it is to be understood that the features of the various embodiments described herein are not mutually exclusive and can exist in various combinations and permutations.

BRIEF DESCRIPTION OF THE DRAWINGS

The accompanying drawings, which are included to provide a further understanding of the embodiments of the present disclosure, are incorporated in and constitute a part of this specification, illustrate embodiments of the present disclosure, and together with the detailed description, serve to explain the principles of the embodiments discussed herein. No attempt is made to show structural details of this disclosure in more detail than can be necessary for a fundamental understanding of the exemplary embodiments discussed herein and the various ways in which they can be practiced. According to common practice, the various features of the drawings discussed below are not necessarily drawn to scale. Dimensions of various features and elements in the drawings can be expanded or reduced to more clearly illustrate the embodiments of the disclosure.

FIG. 1 is a simplified schematic chart illustrating top-level functionality of the ophthalmologic surgical system showing an image processing subsystem, a planning subsystem, a surgical guidance subsystem, and a camera operable coupled to a surgical microscope.

FIG. 2 is an exemplary signal chart schematic illustrating exemplary signals being transmitted and/or received by the respective image processing subsystem, planning subsystem, surgical guidance subsystem, and a camera system of the surgical microscope of the ophthalmologic surgical system of FIG. 1, which allows for the provision, via the surgical guidance subsystem, of a surgical guidance overlay that can be displayed on a video output device. In optional aspects, the display can include the surgical guidance overly, a composition of the surgical guidance overlay and real-time surgical video coming from the camera system, and the like.

FIGS. 5A and 5B are exemplary schematic flowcharts for the methodology of the surgical guidance subsystem of the ophthalmologic surgical system.

DETAILED DESCRIPTION

Figures 1, 2:
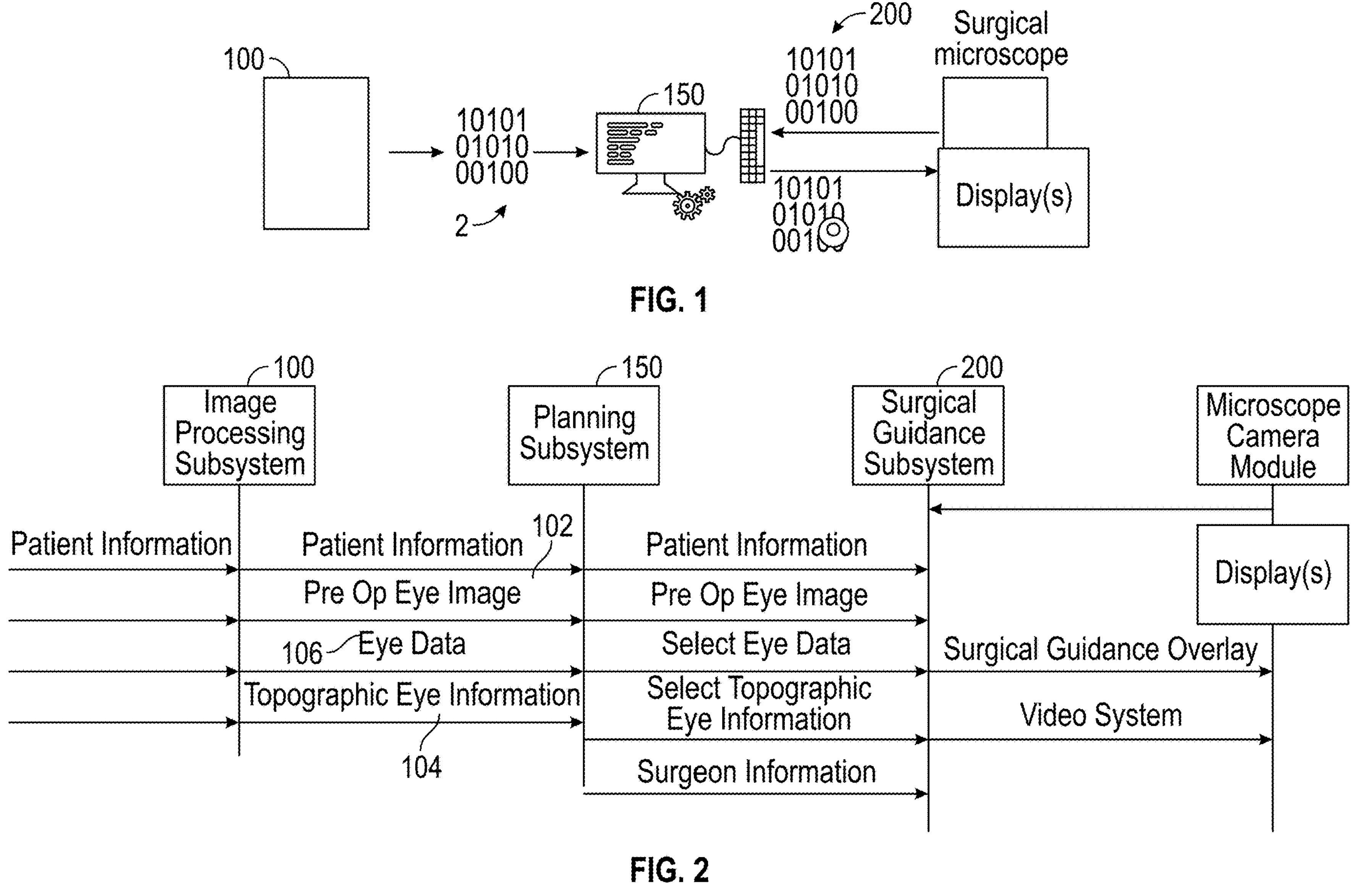

The present invention can be understood more readily by reference to the following detailed description, examples, drawings, and claims, and their previous and following description. However, before the present devices, systems, and/or methods are disclosed and described, it is to be understood that this invention is not limited to the specific devices, systems, and/or methods disclosed unless otherwise specified, and, as such, can, of course, vary. It is also to be understood that the terminology used herein is for the purpose of describing particular aspects only and is not intended to be limiting.

The following description of the invention is provided as an enabling teaching of the invention in its best, currently known embodiment. To this end, those skilled in the relevant art will recognize and appreciate that many changes can be made to the various aspects of the invention described herein, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof.

As used throughout, the singular forms "a," "an" and "the" include plural referents unless the context clearly dictates otherwise. Thus, for example, reference to "a notch" can include two or more such notches unless the context indicates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the terms "optional" or "optionally" mean that the subsequently described event or circumstance can or cannot occur, and that the description includes instances where said event or circumstance occurs and instances where it does not.

The word "or" as used herein means any one member of a particular list and also includes any combination of members of that list. Further, one should note that conditional language, such as, among others, "can," "could," "might," or "can," unless specifically stated otherwise, or otherwise understood within the context as used, is generally intended to convey that certain aspects include, while other aspects do not include, certain features, elements and/or steps. Thus, such conditional language is not generally intended to imply that features, elements and/or steps are in any way required for one or more particular aspects or that one or more particular aspects necessarily include logic for deciding, with or without user input or prompting, whether these features, elements and/or steps are included or are to be performed in any particular embodiment.

As used herein, the unit "pixel" refers to the smallest element in a (digital) (video frame) image of real world objects, which in embodiments represents a real world physical dimension between 3 and 60 micron depending on image acquisition circumstances including, but not limited to, camera sensor type, zoom level and focal distance.

The phraseology and terminology used herein is for the purpose of description and should not be regarded as limiting. As used herein, the term "plurality" refers to two or more items or components. The terms "comprising," "including," "carrying," "having," "containing," and "involving," whether in the written description or the claims and the like, are open-ended terms, i.e., to mean "including but not limited to." Thus, the use of such terms is meant to encompass the items listed thereafter, and equivalents thereof, as well as additional items. Only the transitional phrases "consisting of" and "consisting essentially of," are closed or semi-closed transitional phrases, respectively, with respect to any claims. Use of ordinal terms such as "first," "second," "third," and the like in the claims to modify a claim element does not by itself connote any priority, precedence, or order of one claim element over another or the temporal order in which acts of a method are performed but are used merely as labels to distinguish one claim element having a certain name from another element having a same name (but for use of the ordinal term) to distinguish claim elements.

Disclosed are components that can be used to perform the disclosed methods and systems. These and other components are disclosed herein, and it is understood that when combinations, subsets, interactions, groups, etc. of these components are disclosed that while specific reference to each various individual and collective combinations and permutation of these cannot be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

The present methods and systems can be understood more readily by reference to the following detailed description of preferred embodiments and the examples included therein and to the Figures and their previous and following description.

In various embodiments, as exemplarily shown in FIG. 1, the ophthalmologic surgical system 2 can be configured to enable scanning and imaging of the anatomical and physiological characteristics of the patient's eye via an image processing subsystem 100; to provide, in the planning subsystem 150, for the production of a surgical plan based on imaging and eye data received from the image processing subsystem; and to provide, in a surgical guidance subsystem 200, for accurate surgical guidance that is based on the surgical plans produced by the planning subsystem where such surgical guidance is timely corrected and/or adapted to adjust for movement of the patient's eye in the course of the surgical procedure.

In embodiments, it is contemplated that one or more of the image processing subsystem, the planning subsystem, and the surgical guidance subsystem can use at least one graphical user interface ("GUI") as shown in the figures below. As exemplarily illustrated, the GUI can be displayed on a touch-screen control panel and can feature different types of control screens including, without limitation, administrative screens, planning screens, and surgical guidance screens for user selected surgical procedures. In this aspect, it is contemplated that the GUI and the touch-screen control panel can be configured to enable the user to press a respective portion of the touch-screen control panel to either navigate within the GUI, initiate the entry of data for the parameter listed at the selected portion of the touch-screen control panel, or initiate a process within the selected surgical procedure.

In embodiments, the image processing subsystem 100 can be configured to enable scanning and imaging of the anatomical and physiological characteristics of the patient's eye, which can include, for example, without limitation, color imaging of the patient's eye and topographic measurements of the patient's eye including anterior and posterior surfaces of the cornea and the lens and lens capsule. The planning subsystem 150 is configured to generate treatment and surgical guidance planning and can selectively receive imaging, such as, for example and without limitation, a full color image of the patient's eye, and topographic anatomical and physiological characteristics of the patient's eye. Based on the received topographic eye information and the eye image, the planning system is configured to generate surgical plans and to verify desired eye orientation and planned surgical incisions prior to initiation of a guided surgical procedure on the patient's eye.

In embodiments, it is contemplated that the planning subsystem 100 could make use of machine learning models to learn from previous planned cases and surgeon preference to suggest optimized surgical plans, which can streamline the planning process and can increasing the overall success rate by using best known strategies.

In further optional embodiments, the planning subsystem could dynamically adjust its graphical user interface to allow for personalized customization tailored to the surgeon or surgery practice. For instance, by hiding certain lens types based on availability or commercial constraints.

In a further embodiment, the surgical guidance subsystem 200 can be configured to provide at least one of: patient verification, treatment surgical plan verification, registration of a real-time video image of the patient's eye as displayed to the surgeon via the surgical microscope to the image of the patient's eye that was provided by the planning subsystem; provision of surgical guidance imaging in a visual overlay throughout the surgical procedure in accord with the selected, planned surgical procedure; tracking identified "features" or "landmarks" on the patient's eye after eye registration to ensure accurate registration of the provided surgical guidance relative to the patient's eye and irrespective to movement of the patient's eye throughout the surgical procedure.

In various exemplary embodiments, select elements of an embodiment of an image processing subsystem 100 can include a processor coupled via shared bus to memory media (collectively identified as memory). The image processing subsystem 100 can further include a communication interface that can interface the image processing subsystem 100 to various external entities, such as a network or the planning subsystem, and a display interface configured to connects shared bus, or another bus, with an output port for one or more displays. As contemplated, the image processing subsystem 100 can further include a camera interface for acquisition of eye images from a camera included in the image processing subsystem.

In various embodiments, the image processing subsystem 100 can be integrated with different types of equipment. In one exemplary embodiment, the image processing subsystem 100 can be integrated with the planning subsystem 150. In one exemplary aspect, the image processing subsystem 100 can be a Cassini Ambient imaging system, manufactured by Cassini Technologies B.V., Anna van Buerenplein 40A, 2595DA, The Hague, The Netherlands. Modifications, additions, or omissions can be made to the image processing subsystem 100 without departing from the scope of the disclosure. The components and elements of the image processing subsystem 100, as described herein, can be integrated or separated according to particular applications. It is also contemplated that the image processing subsystem 100 can be implemented using more, fewer, or different components in some embodiments.

Figure 3:
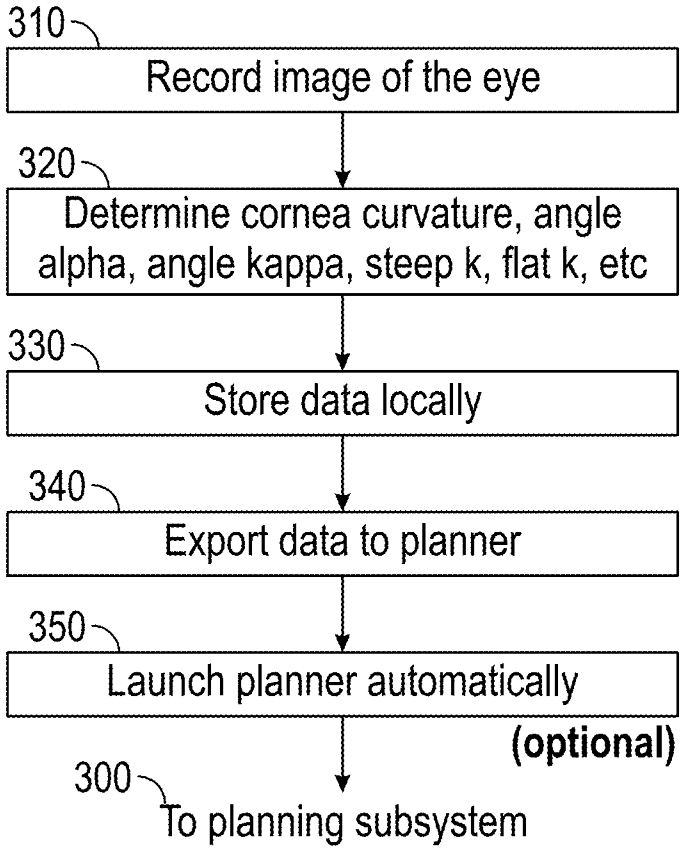
FIG. 3 is an exemplary schematic flowchart for the methodology of the image processing subsystem of the ophthalmologic surgical system.

In embodiments and referring to FIGS. 2 and 3, the image processing subsystem 100 can be configured to generate data that can be transmitted to the planning subsystem 150 for the production of a patient surgical plan. In a non-limiting example, the data generated by the image processing subsystem can include, without limitation, one or more of: a preoperative image of the eye 102, a pixel to mm conversion factor for the image processing subsystem; and topographic eye data 104. In exemplary aspects, the preoperative image of the eye 102 can be, without limitation, a color image of the eye, an infra-red image of the eye, a topographic map, or the like.

Exemplary topographic eye data 104 can include, without limitation (to include no limitation on the noted unit of measurement (e.g., Diopter)), one or more of: sagittal/Axial map data; anterior keratometric power data for steep axis in Diopter; anterior axis value data for steep axis in degrees; posterior keratometric power data for steep axis in Diopter; posterior axis value data for steep axis in degrees; Total Corneal Astigmatism (TCA) keratometric power data for steep axis in Diopter; TCA axis value data for steep axis in degrees; anterior keratometric power data for flat axis in Diopter; anterior axis value data for flat axis in degrees; anterior keratometric power data for flat axis in Diopter; posterior axis value data for flat axis in degrees; TCA keratometric power data for flat axis in Diopter; TCA axis value data for flat axis in degrees; and the like.

Further, it is contemplated that the image processing subsystem 100 can generate additional topographic eye data 104 in the form of eye characterization data 106 that can include, without limitation (to include no limitation on the noted unit of measurement (e.g., pixels)), one or more of: limbus description data (e.g. including without limitation the limbus as an ellipse in pixels); pupil description data (e.g. including without limitation the pupil boundary as an ellipse in pixels); the x, y coordinates in pixels of the visual axis; the distance in mm from the center of the limbus to the visual axis, and the angle from the center of the limbus to the visual axis in degrees, (where the x-axis is 0 and y-axis is 90), together describing angle alpha; the equivalent diameter of the limbus; the distance in mm from the center of the mesopic pupil to the visual axis, and the angle from the center of the mesopic pupil to the visual axis in degrees (where the x-axis is 0 and y-axis is 90), together describing mesopic angle kappa; the equivalent diameter of the mesopic pupil area; the distance in mm from the center of the photopic pupil to the visual axis, and the angle from the center of the photopic pupil to the visual axis in degrees (where the x-axis is 0 and y-axis is 90), together describing photopic angle kappa; the equivalent diameter of the photopic pupil area; and the like. In embodiments, it is contemplated that the eye data 104, and any eye characterization data 106, can be transmitted or otherwise communicated to the planning subsystem 150 prior to initiation of the surgical planning operation.

In embodiments and referring to FIG. 3, an exemplary schematic flowchart for the methodology 300 of the image processing subsystem 100 of the ophthalmologic surgical system is illustrated. It will be appreciated that method 300 is an exemplary embodiment of a method employed in accordance with techniques described herein. Method 300 can be modified to facilitate variations of its implementations and uses. Method 300 can be implemented in software, hardware, or a combination thereof. The order of method 300 can be changed, and various elements may be added, reordered, combined, omitted, modified, etc.

In embodiments and referring to FIG. 3, as shown in step 310, the image processing subsystem 100 is configured to record at least one full color image 102 of the patient's eye. In embodiments, this full color image 102 can be a still image taken with a conventional camera or can be a still frame color image taken from or otherwise selected from a video stream. Concurrently or sequentially, the image processing subsystem 100 also determines topographic eye data 104, as identified above, in step 320. This topographic eye data can be stored locally in the image processing subsystem 100 in step 330. Optionally, and without limitation, it is contemplated that the determined eye data can also be stored remotely, such as in a network server, the cloud and the like.

As noted, the image processing subsystem 100 is configured to be selectively placed in communication with the planning subsystem 150. Thus, upon selection by the user, the topographic eye data 104 and the at least one color image 102 of the patient's eye can be exported or otherwise transferred to the planning subsystem 150 from the image processing subsystem 100 in step 340. In an optional step shown as 350, upon selection of the user to export the eye data 104 and the at least one color image 102 of the patient's eye, the planning subsystem can be commanded to initiate operations.

The planning subsystem 150 is configured to generate treatment and surgical guidance planning and can selectively receive imaging, such as, for example and without limitation, a full color image of the patient's eye 102, and anatomical and physiological characteristics of the patient's eye. Based on the received eye information and the eye image 102, the planning system is configured to generate surgical plans and to verify desired eye orientation and planned surgical incisions prior to initiation of a guided surgical procedure on the patient's eye.

Modifications, additions, or omissions can be made to the planning subsystem 150 without departing from the scope of the disclosure. The components and elements of the planning subsystem 150, as described herein, can be integrated or separated according to particular applications. It is also contemplated that the planning subsystem 150 can be implemented using more, fewer, or different components in some embodiments.

The planning subsystem 150 can be used by users to create and edit treatment templates and to create, edit, and initiate treatment plans. In operation, the planning screens can allow a user to verify the identity of a patient, to receive a color image 102 of the eye from an image processing subsystem 100, to receive at least one measured anatomical and physiological eye information data (topographic data 104) associated with the eye from the image processing subsystem image, and to plan, customize and verify surgical treatment plans and treatment parameters.

Figure 4:
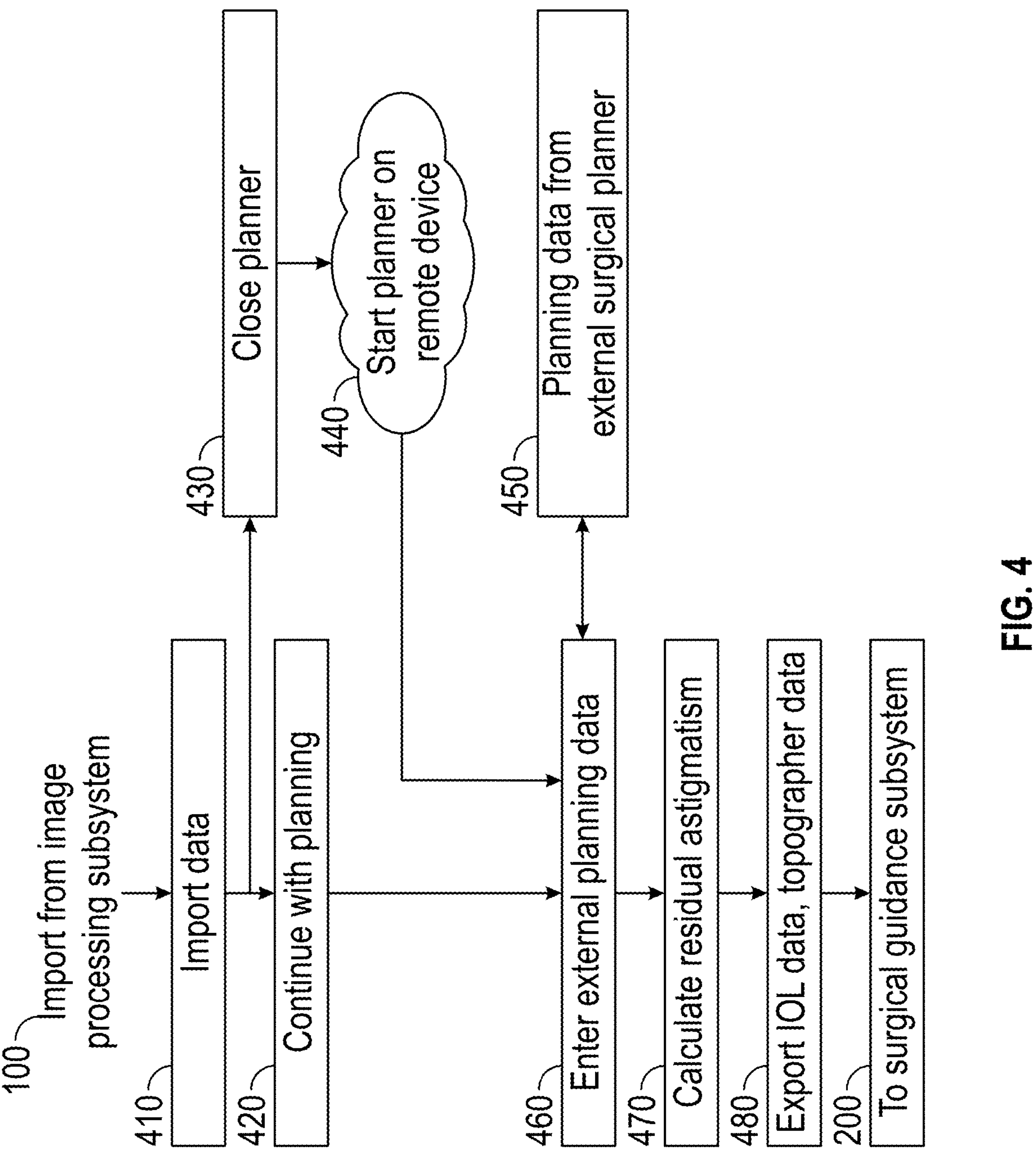
FIG. 4 is an exemplary schematic flowchart for the methodology of the planning subsystem of the ophthalmologic surgical system.

In embodiments and referring to FIG. 4, an exemplary schematic flowchart for the methodology 400 of the planning subsystem of the ophthalmologic surgical system is illustrated. It will be appreciated that method 400 is an exemplary embodiment of a method employed in accordance with techniques described herein. Method 400 can be modified to facilitate variations of its implementations and uses. Method 400 can be implemented in software, hardware, or a combination thereof. The order of method 400 can be changed, and various elements may be added, reordered, combined, omitted, modified, etc.

In embodiments and referring to FIG. 4, the user can input surgical profile information 152 into the planning subsystem 150 in step 420. In various aspects, such surgical profile information 152 can include, without limitation, one or more of: the desired sitting position for the operating physician (e.g., Superior or Temporal); a desired Phaco technique (e.g., coaxial or bimanual); a centration preference (e.g., visual axis or angle alpha); the desired size of the clear corneal incision in mm; the desired paracentesis size in mm; the desired angle of the center of the paracentesis in degrees relative to the 0-axis determined by preop registration; any desired incision correction for cyclorotation; any surgical induced astigmatism; the desired capsulotomy diameter in mm; a desired overlay color scheme for the guidance module; and the like.

In embodiments, it is contemplated that surgical profile information 152 can include surgical plan data 154, which can include, without limitation, one or more of; the IOL manufacturer and model name; the spherical equivalent (SE) power (in Diopter) of the IOL in the IOL plane; the cylindrical power (in Diopter) of the IOL in the IOL plane; the cylindrical power (in Diopter) of the IOL in the corneal plane; the angle of IOL axis relative to relative to the 0-axis determined by preop registration (which is typically close to TCA axis); the predicted residual astigmatism based on calculator in diopter; the Angle of the predicted residual astigmatism in degrees; the keratometric steep power used in planner in diopter (which can be potentially adjusted); the keratometric steep axis used in planner in deg (which can be potentially adjusted); the keratometric flat power used in planner in diopter (which can be potentially adjusted); the keratometric flat axis used in planner in deg (which can be potentially adjusted); and the like.

In various exemplary embodiments, it is contemplated that surgical plan data 154 can include selectable surgical incision positions 156 that can be used in the planning subsystem can include, without limitation, at least one of: capsulotomy incisions, lens fragmentation incisions, cataract incisions, and arcuate incisions. Such surgical incision positions 156 can be preplanned, i.e., positioned in accord with surgeon's inputted preferences for a particular surgical procedure; suggested, i.e., positioned by the surgical guidance subsystem 200 in "suggested" positions for a particular surgical procedure; or manually positioned by the surgeon via the surgical panning subsystem 150. In the manual mode, it is contemplated that any preplanned or suggested incision positions can be manually positioned by the surgeon in the course of the creation of the surgical plan via the surgical planning software. A capsulotomy incision is often planned to be formed in the anterior portion of the lens capsule so as to provide access to a cataractous lens nucleus for removal of the cataractous lens nucleus.

In step 420, the user elects to continue with surgical planning. In an optional step 430, the user can close the planning subsystem 150 and reopen the planning subsystem 150 on a remote device 440, which can be coupled to the planning subsystem via a network or cloud communication system. Planning data 154, stored on an external surgical planner in step 450, can be inputted or entered into the planning subsystem 150 in step 460. In step 470, residual astigmatism is determined for the patient's eye based on the supplied surgical plan data 154. Finally, in step 480, data generated by the planning subsystem 150 can be selectively exported to the surgical guidance subsystem 200.

In a further embodiment, the surgical guidance subsystem 200 can be configured to provide at least one of: patient verification, treatment surgical plan verification, registration of a real-time video image of the patient's eye as displayed to the surgeon via the surgical microscope to the image of the patient's eye that was provided by the planning subsystem; provision of surgical guidance imaging in a visual overlay throughout the surgical procedure in accord with the selected, planned surgical procedure; tracking identified "features" or "landmarks" on the patient's eye after eye registration to ensure accurate registration of the provided surgical guidance relative to the patient's eye and irrespective to movement of the patient's eye throughout the surgical procedure. As one will appreciate, it is contemplated that surgical guidance GUI screens can be used to edit, initiate, and monitor selected planned treatment plans.

Modifications, additions, or omissions can be made to the surgical guidance subsystem 200 without departing from the scope of the disclosure. The components and elements of the surgical guidance subsystem 200, as described herein, can be integrated or separated according to particular applications. It is also contemplated that the surgical guidance subsystem 200 can be implemented using more, fewer, or different components in some embodiments.

In aspects, the surgical guidance subsystem 200 of the ophthalmologic surgical system can be operable to show the user, in a visual overlay of the surgical field, the preplanned desired location of a circular opening in the anterior portion of the lens capsule. Lens fragmentation incisions are typically planned to be formed in the cataractous lens nucleus so as to allow for the fragmentation of the lens into small portions to aid in the removal of the lens nucleus. Further, cataract incisions are conventionally planned to be formed in the cornea to provide access for surgical tools used to remove the fragmented lens nucleus and through which an IOL can be passed for implantation to provide optical function compensating for the absence of the lens nucleus. A conventional cataract incision can include primary incisions, which are typically large enough that an IOL can be inserted through the primary incision as well as surgical instruments can be used during cataract replacement surgery, and secondary (or "side port") incisions, that are smaller than the primary incisions and through which surgical instruments can be used during cataract replacement surgery can be inserted. Finally, arcuate incisions are generally planned to be made in the cornea and can be used to reshape the cornea, thereby modifying the optical properties of the cornea.

Figure 5B:
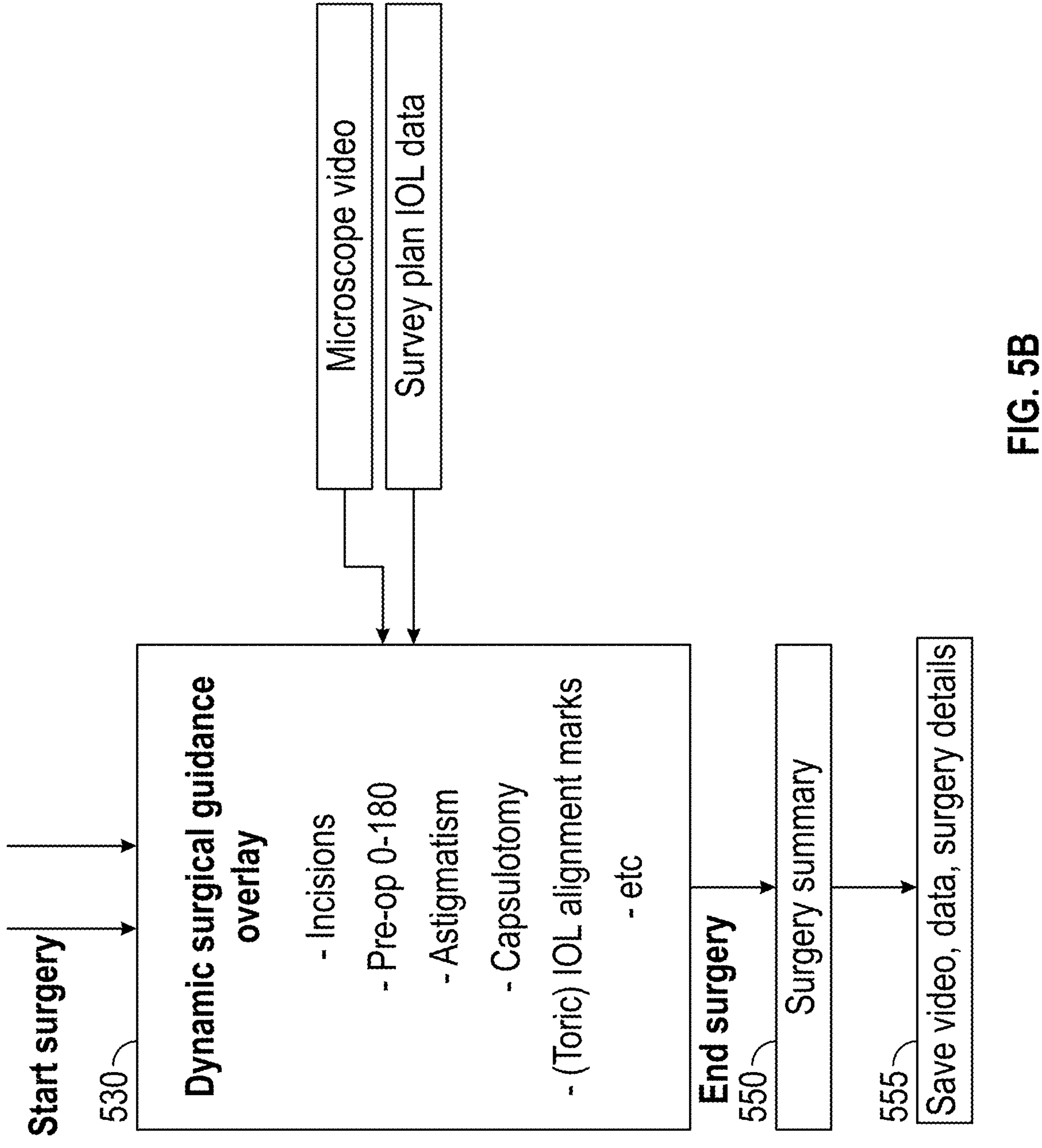

In embodiments and referring to FIGS. 5A and 5B, an exemplary schematic flowchart for the methodology 500 of the surgical guidance subsystem 500 of the ophthalmologic surgical system is illustrated. It will be appreciated that method 500 is an exemplary embodiment of a method employed in accordance with techniques described herein. Method 500 can be modified to facilitate variations of its implementations and uses. Method 500 can be implemented in software, hardware, or a combination thereof. The order of method 500 can be changed, and various elements may be added, reordered, combined, omitted, modified, etc.

As noted above, in step 480, the data generated by the planning subsystem 150 can be selectively exported to the surgical guidance subsystem 200. Subsequently, in step 505, the surgeon can initiate the surgical examination with a general visualization of the patient's eye through visualization of the video stream generated by the surgical microscope. In step 510, the surgeon can review the imported data that was supplied by the planning subsystem 150 and subsequently can, in step 515, initiate recording of the surgical procedure.

In step 515, the registration process can be initiated by the surgeon. The registration process ensures that the diagnostic data generated by the planning subsystem 20 for the patient's eye is "registered" or otherwise correctly oriented to the view of the patient's eye as seen in the surgical microscope video stream—this registration allows for the correct orientation of a guidance overlay that is superimposed over the view of the patient's eye as seen in the surgical microscope video stream. The surgeon can, in step 525, bypass the automatic registration process described below to effect a manual registration of the full color image 102 provided by the image process subsystem 100 and a video frame image that was selected from the microscope video stream. After registration, and discussed in more detail below, a tracking process is subsequently used to ensure the accuracy of the position of the overlay relative to the microscope video stream throughout the surgical procedure.

Figure 6A:
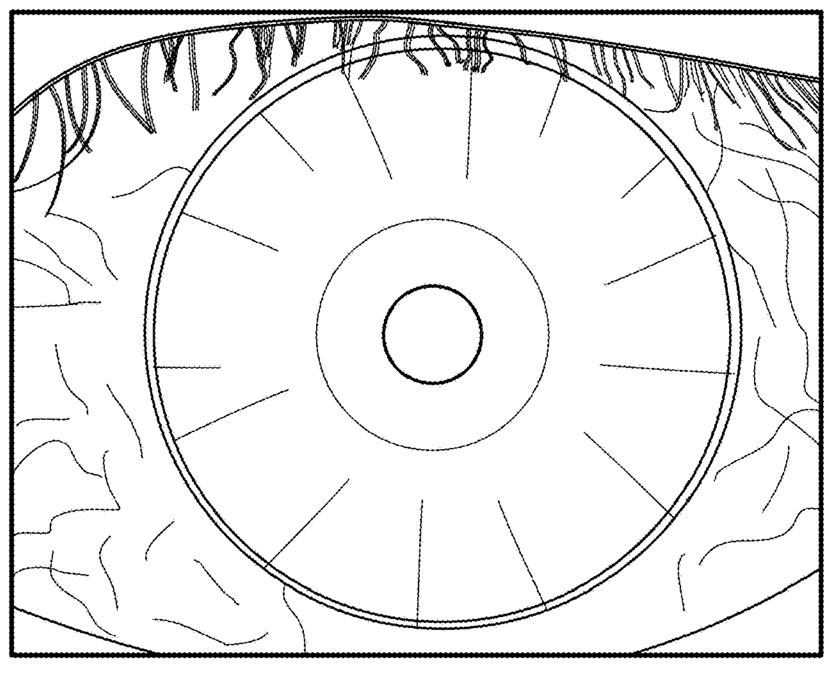
FIG. 6A shows an image of the eye generated in the image processing subsystem, and showing pupil and limbus overlays.
Figure 6B:
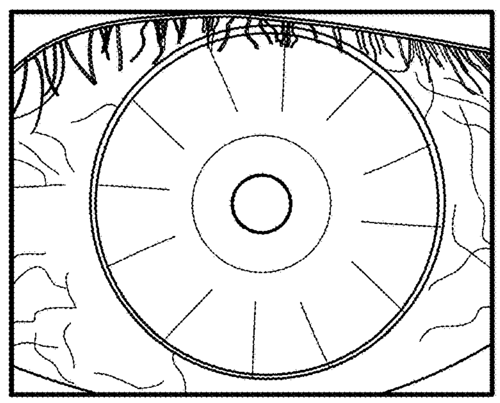
FIG. 6B shows an image provided by the image process subsystem and FIG. 6C shows a video frame image that was selected from the microscope video stream.

In embodiments, a pair of eye images, examples of which are depicted in FIGS. 6A and 6B, is used in the registration process. FIG. 6A shows a full color image 102 of the eye generated in the image processing subsystem and FIG. 6B shows a video frame image selected from the surgical microscope video stream.

Conventionally, video frame images can have an interlaced format and can have about 1920×1080 pixels. Other pixel resolutions are contemplated, but the following disclosure will be based on an image having 1920×1080 pixels. One skilled in the art can modify the described process to effect the desired result for an image having a differing pixel format.

In an exemplary step, the iris can be detected in the video frame image as the region between the pupil boundary and the limbus, via techniques including, but not limited to, de-interlacing, down-sampling, noise removal, edge detection, region growing and shape fitting. In embodiments, the fitted shapes can be elliptic.

Figure 6C:
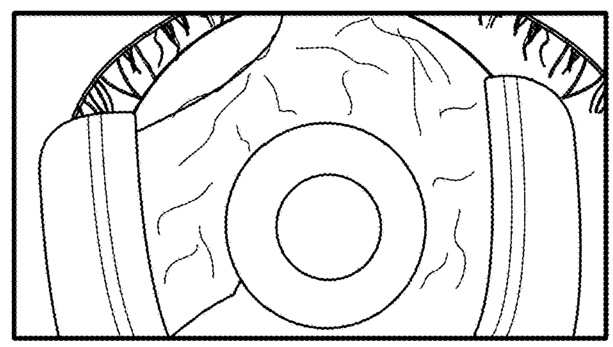
Figure 6D:
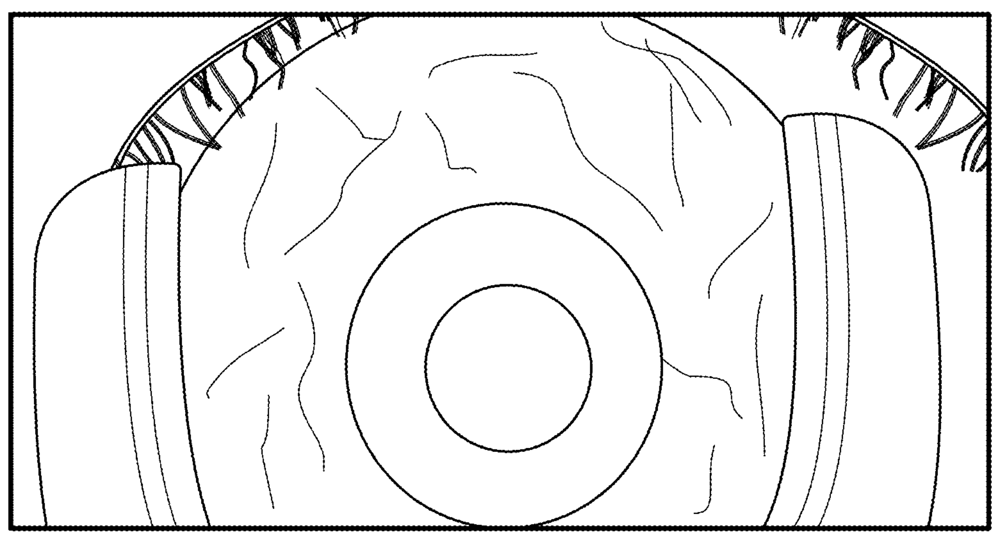
FIG. 6D shows an aggressively down sampled video frame image.
Figure 6E:
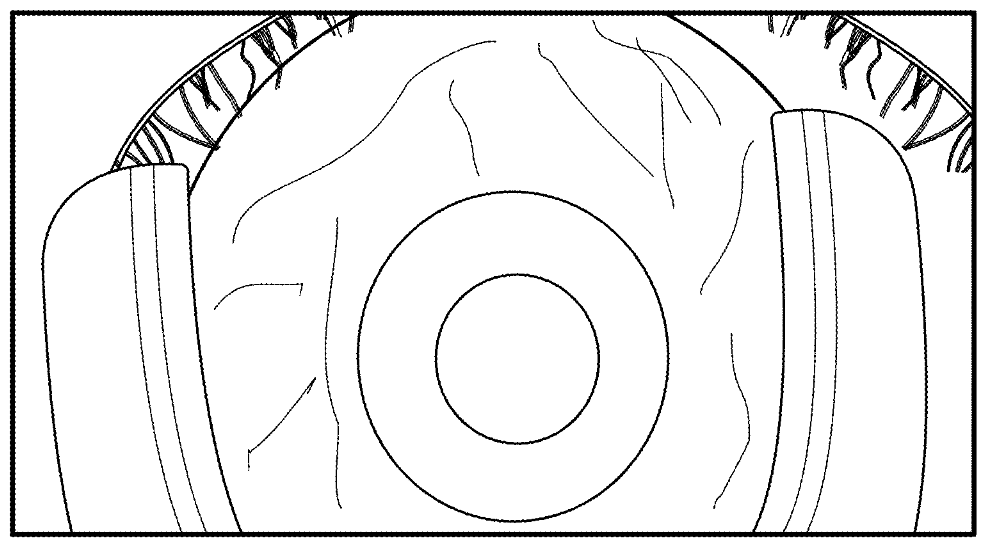
FIG. 6E less aggressively down sampled video frame image.
Figure 6F:
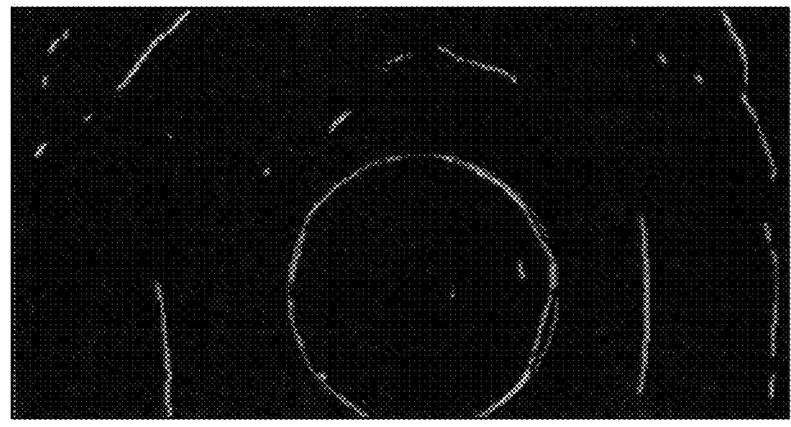
FIGS. 6F-6H show the limbus as a circle (FIG. 6F); as an ellipse (FIG. 6G); and projected onto the full color image (FIG. 6H) generated from the video stream of the surgical microscope.
Figure 6G:
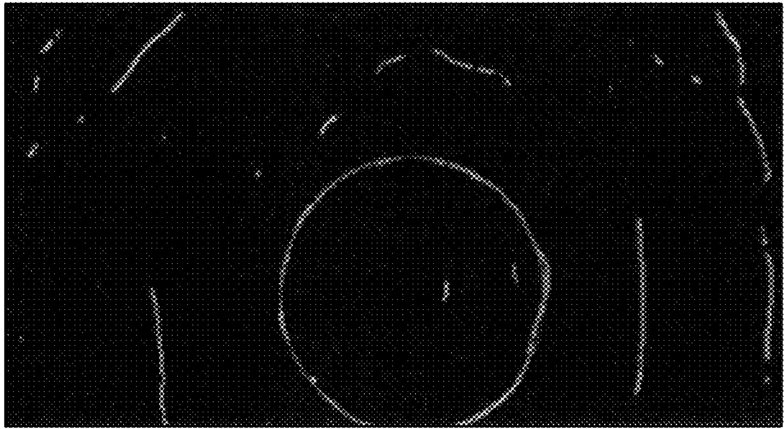
Figure 6H:
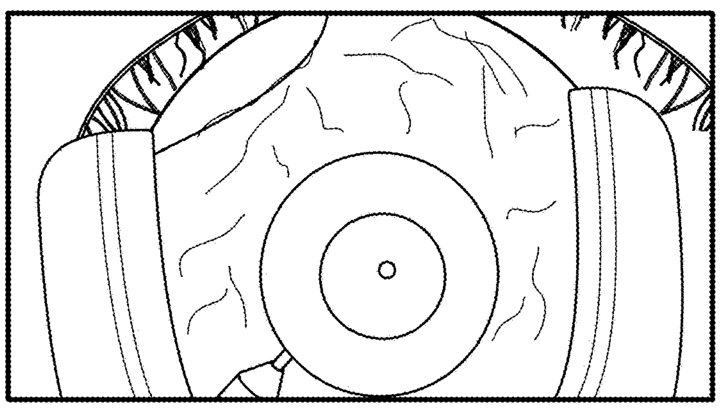
Figure 6J:
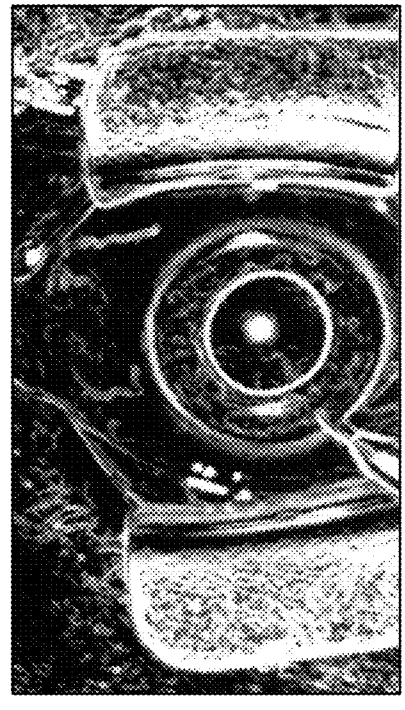
FIGS. 6I-6L show a down sampled RGB (two times down sampled, FIG. 6I); a gradient magnitude (FIG. 6J); a local gradient maxima (FIG. 6K); and a radially outward/inward gradients only, inside limbus (FIG. 6L).
Figure 6L:
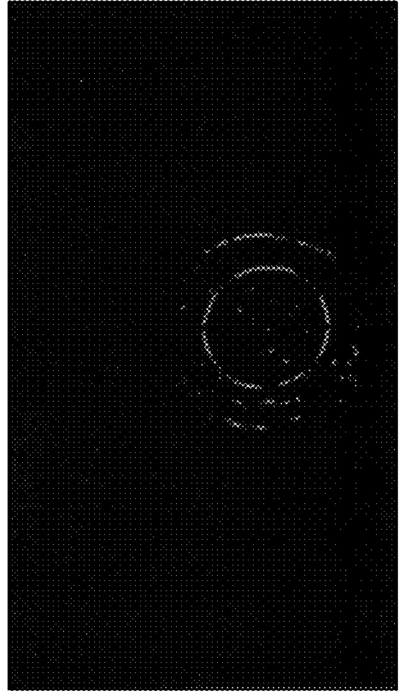
Figure 6I:
Figure 6K:
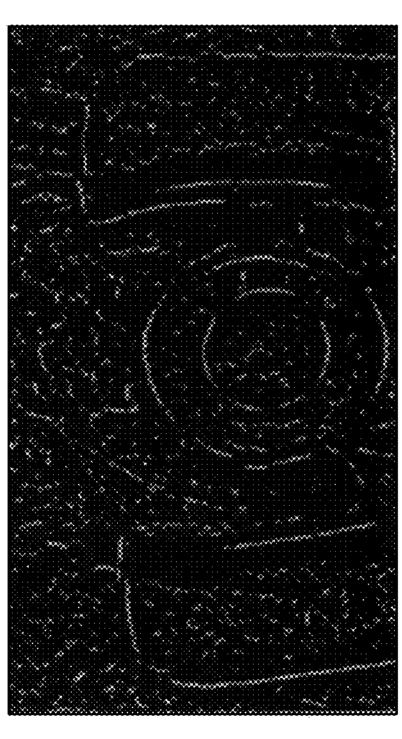
Figure 6O:
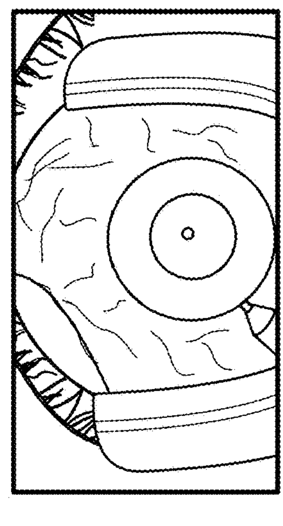
FIGS. 6M-6O show the pupil as a circle (FIG. 6M); as an ellipse (FIG. 6N); and shows the pupil and limbus projected on the video stream of the surgical microscope (FIG. 6O).
Figure 6N:
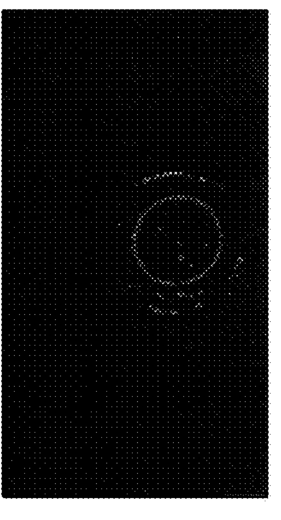
Figure 6M:
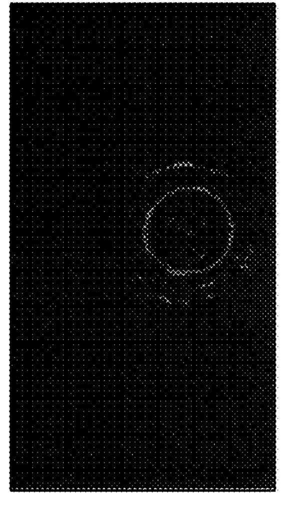
Figure 6Q:
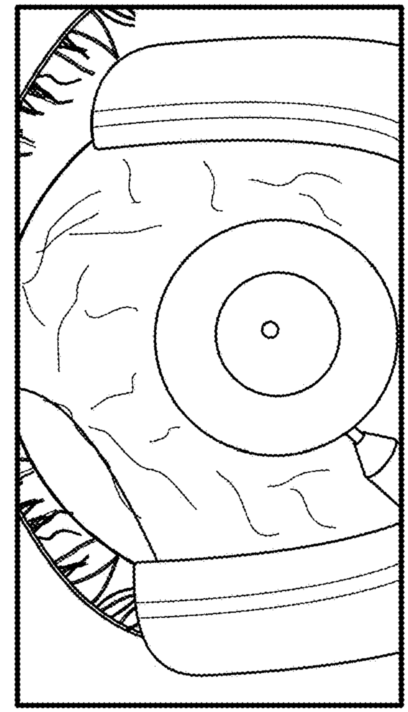
FIGS. 6P-6Q show iris segmentation for the full color image provided by the image process subsystem (FIG. 6P) and the video frame image that was selected from the microscope video stream (FIG. 6Q).
Figure 6P:
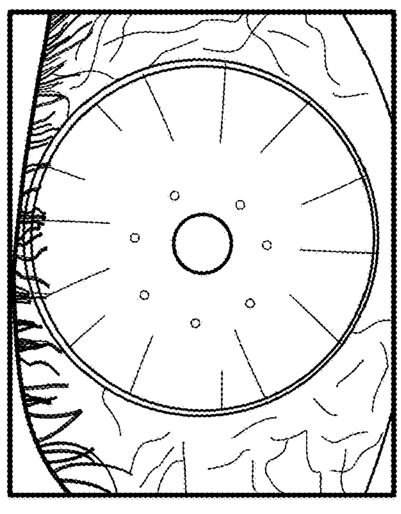
Figure 6R:
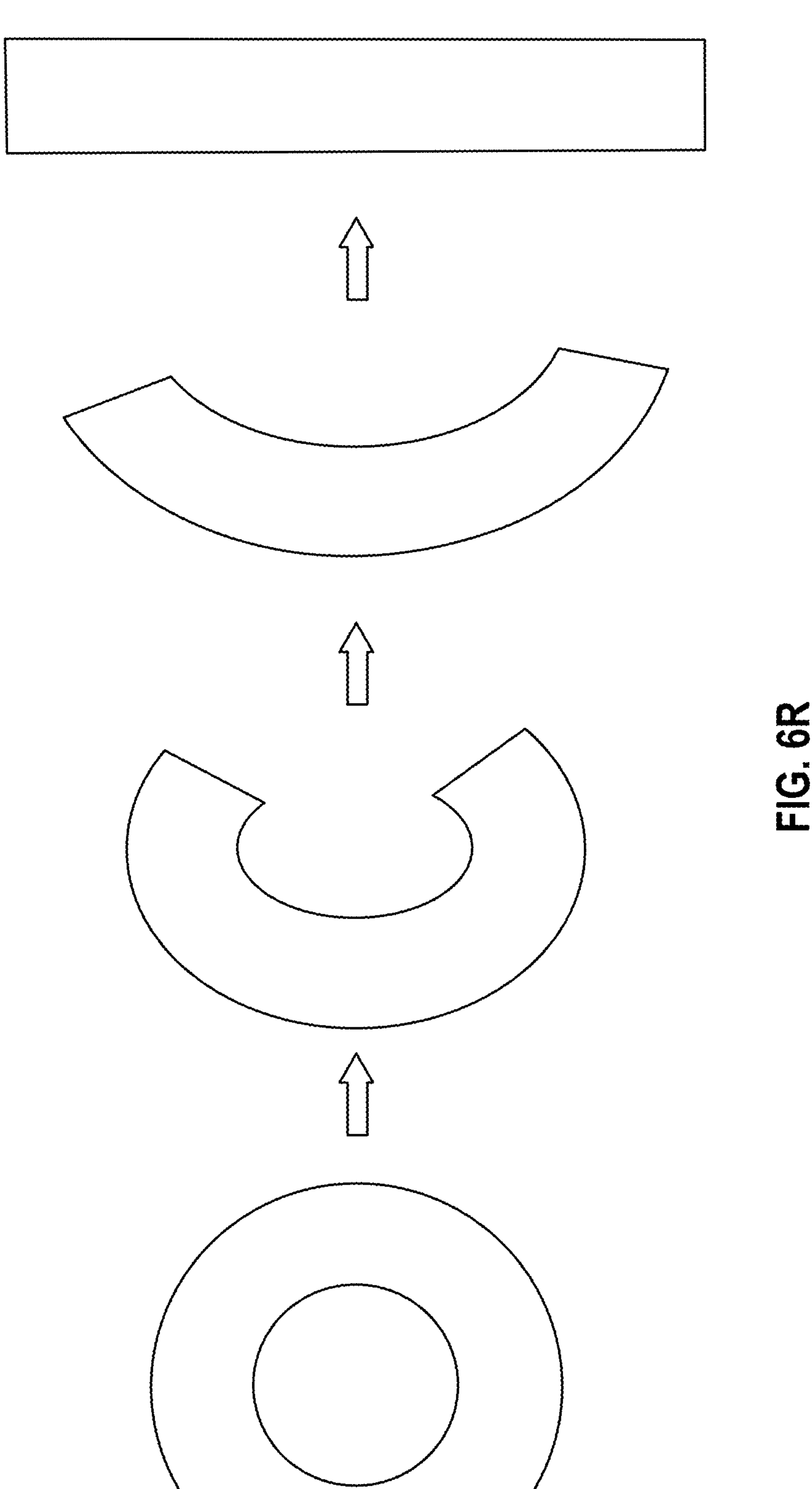
FIG. 6R shows a schematic illustration of the process of unwrapping the irises provided by the image process subsystem and the video frame image that was selected from the microscope video stream.
Figure 6S:
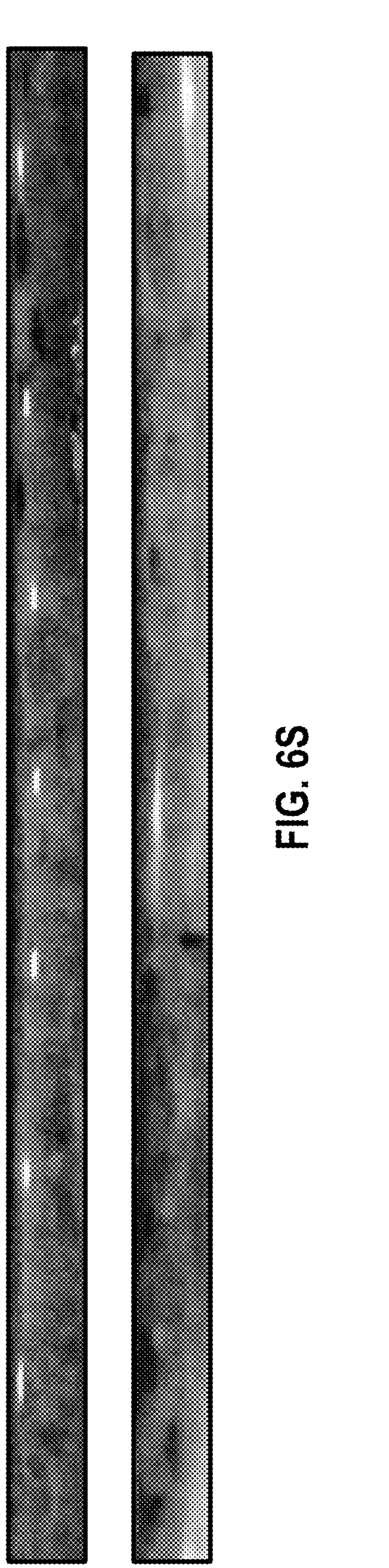
FIG. 6S shows unwrapped irises for the full color image provided by the image process subsystem (top) and the video frame image that was selected from the microscope video stream (bottom).
Figure 6T:
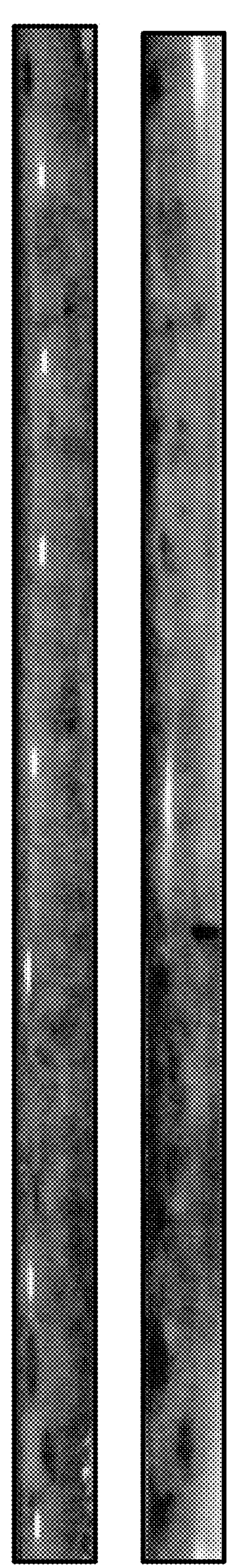
FIG. 6T shows unwrapped irises for the full color image provided by the image process subsystem (top) shifted relative to the video frame image that was selected from the microscope video stream (bottom) to register the respective iris features.

At this point in the registration process and as shown in FIGS. 6C and 6D, the pupil and limbus descriptions are defined in both the full color image 102 provided by the image process subsystem 100 and the video frame image that was selected from the microscope video stream. In embodiments, and as shown in FIG. 6E, the iris region from both images can be unwrapped via an unwrapping scheme. Metrics of correlation between the unwrapped irises can be calculated, and, as shown in FIGS. 6F-6G, the unwrapped full color image provided by the image process subsystem can be "rotated" (e.g., the unwrapped full color image provided by the image process subsystem is laterally shifted) in accord with a calculated peak correlation location, which effects a registration of the irises, and therewith of the two respective images.

Figure 7A:
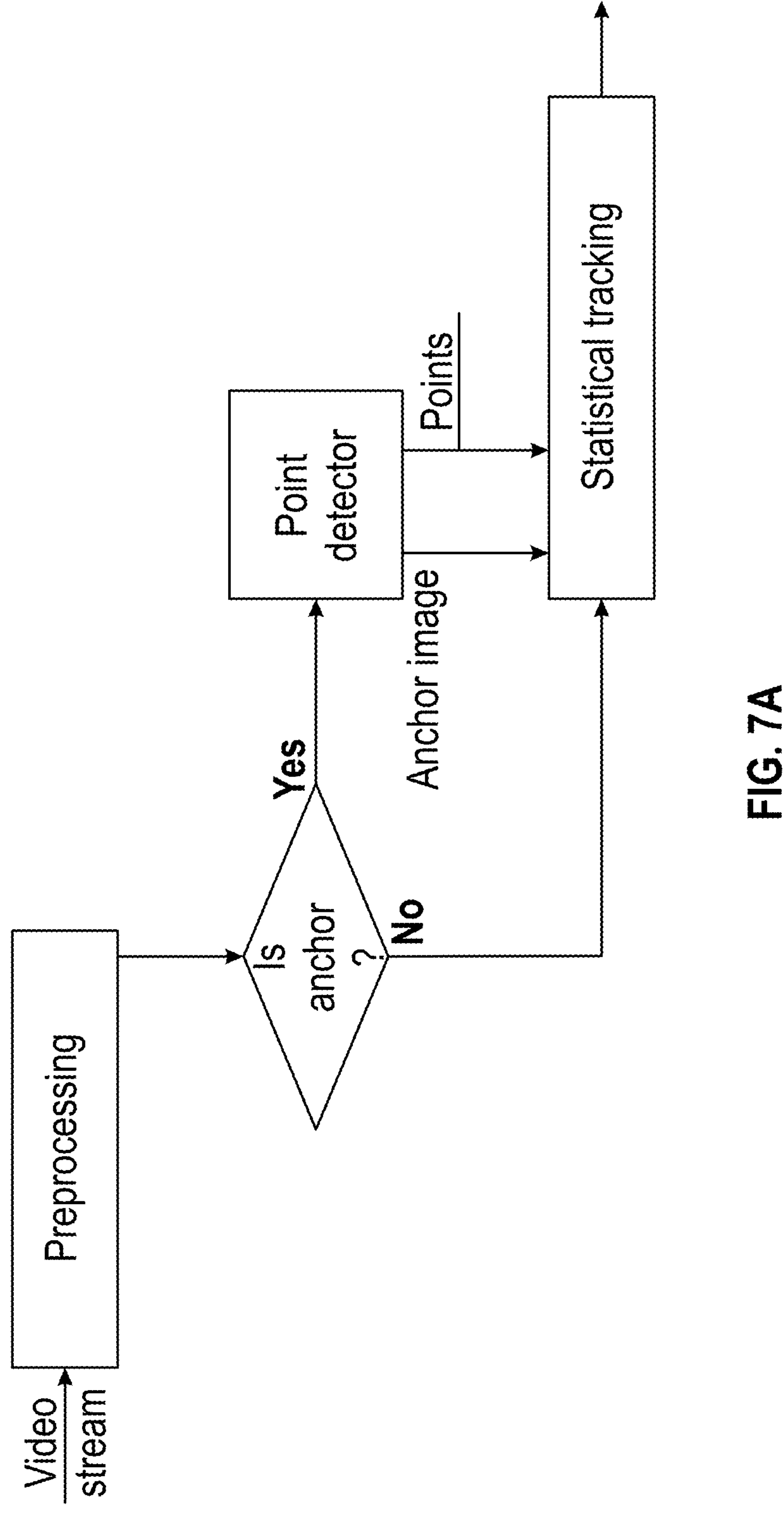
FIG. 7A shows an exemplary schematic flowchart for the methodology of tracking in the surgical guidance subsystem of the ophthalmologic surgical system.

In embodiments and after registration, a tracking process is used to ensure the accuracy of the positioning of a surgical guidance overlay relative to the microscope video stream throughout the surgical procedure. In operation and as schematically shown in FIG. 7A, it is contemplated that the displayed overlays are updated continually in a tracking process to compensate for eye movement and keep the displayed overlays properly aligned with the eye. In embodiments, it is contemplated that the displayed overlays can be updated continually at a frequency sufficient to maintain accurate alignment with the eye's position, which frequency allows the system to effectively compensate for rapid eye movements and maintain the precision required for surgical accuracy. In this aspect, it is contemplated that the overlays can be updated between about every 15 to 70 milliseconds, preferably about between every 20 to 65 milliseconds, and more preferably between about every 28.5 to 50 milliseconds.

In embodiments, the tracking process can estimate eye movement by matching distinctive, and consistent "landmarks" or "features" from incoming frames to those that were identified in an "anchor frame". The landmarks or features are identified by the surgical guidance subsystem 200 using the video frame image that was also used in the registration process.

The "landmarks" or "features" are statistically distinctive sets of pixels that show a unique pattern that consistently appears between different frames. To illustrate, a feature can be any set of pixels that has an identifiable shape, texture, or structure such that the pixel values produce, for example, a high standard deviation in the spatial intensity domain, the presence of zero crossings of the Laplacian of the image intensity, large eigen-value response of the image intensity gradient. The preferred landmarks or features in general should be resolvable between frames using statistical and/or data fitting methods, e.g., least squares, gradient descent, random sample consensus methods. This is achieved by using a dissimilarity that estimates the residue between the features of the anchor and the current frame. When the dissimilarity grows too large the feature is temporarily discarded until the dissimilarity is small enough to include the feature in the matching process. In one exemplary aspect, the preferred landmarks or features can include shapes or structures in the eye that form a substantially "corner" shape or structure (e.g., the intersection of two veins), a particular texture pattern, (e.g. a cluster of scleral vessels).

In embodiments, it is preferred that a plurality of landmarks or features can be identified for tracking purposes. As one will appreciate, as the patient's eye moves during surgery, portions of the eye can become obscured or blocked—thus, it is desired to have a sufficient number of identified landmarks or features on the patient's eye such that, even if a portion of the identified landmarks or features in the patient's eye become blocked, a sufficient number of landmarks or features remain visible and trackable so that the confidence in the determined movement of the eye and the corresponding movement of the displayed overlays remains high. It is also desirable that the plurality of identified landmarks or features are dispersed over the patient's eye.

In various embodiments, it is contemplated that the number of identified landmarks or features can be at least 5, at least 10, at least 50, at least 100, at least 200, or at least 300. It is also contemplated that the number of identified landmarks or features can be between about 5 to about 100, between 50 to about 200, or between 100 to 300. In further embodiments, the number of identified landmarks or features can be between 100 to 1000, or 150 to 500.

Figure 7B:
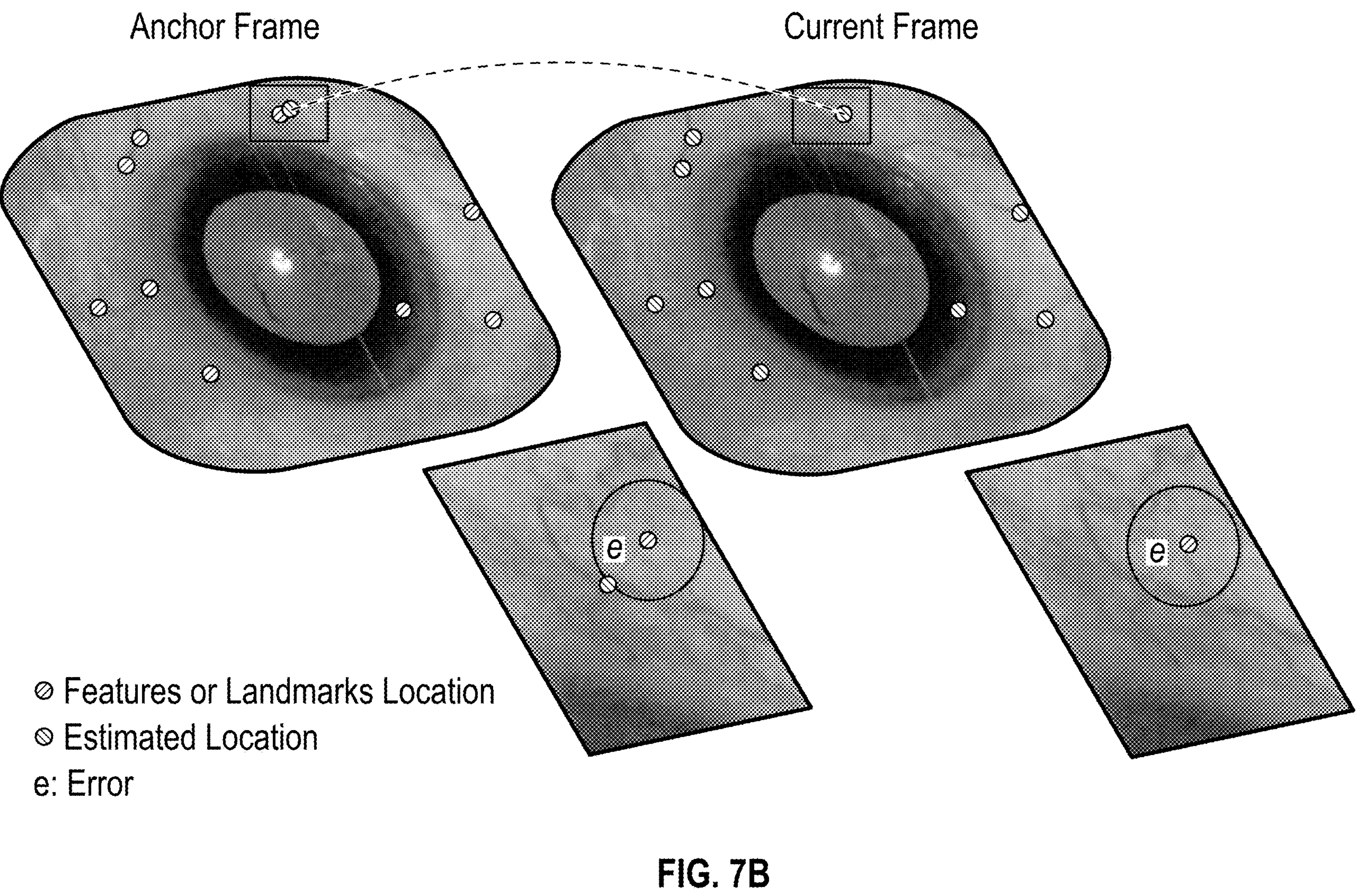
FIG. 7B shows an exemplary schematic illustration of comparisons of identified "features" or "landmark" between a first video frame and a second in time video frame (taken from the video stream generated by the surgical microscope).
Figure 8B:
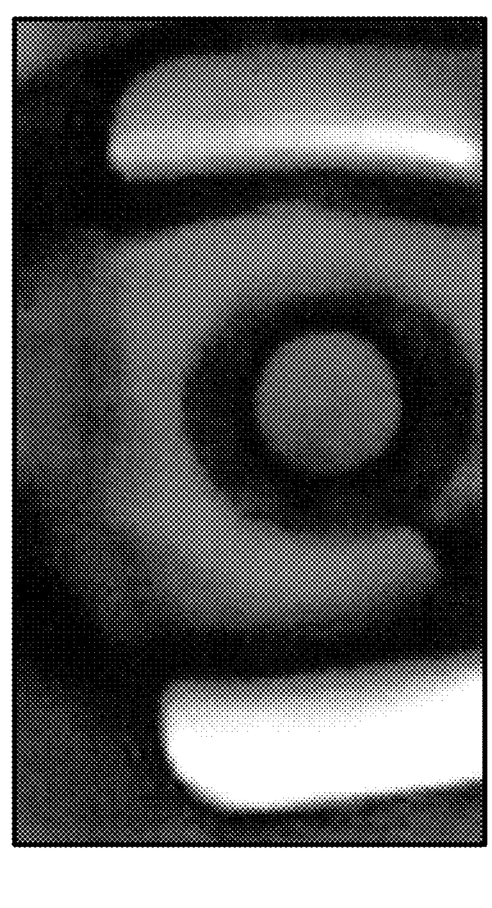
FIG. 8A shows an exemplary video frame image after downscaling and FIG. 8B shows an exemplary video frame image after median filtering in the sclera characterization process so that landmarks or features can be identified for eye movement tracking.
Figure 8D:
FIG. 8C shows a gradient magnitude image and FIG. 8D shows a binary image representing the gradient magnitude local maxima. These images are obtained by enhancing the edges (sharp color transitions) of the median filtered image by calculating the gradient magnitude. In this aspect, the local maxima along the gradient direction (within a window of 3 pixels) can be detected as the edges.
Figure 8A:
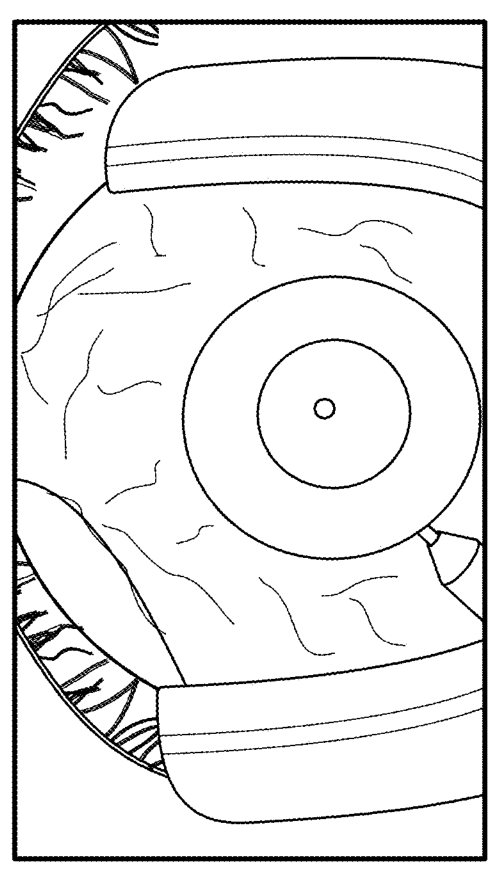
Figure 8C:
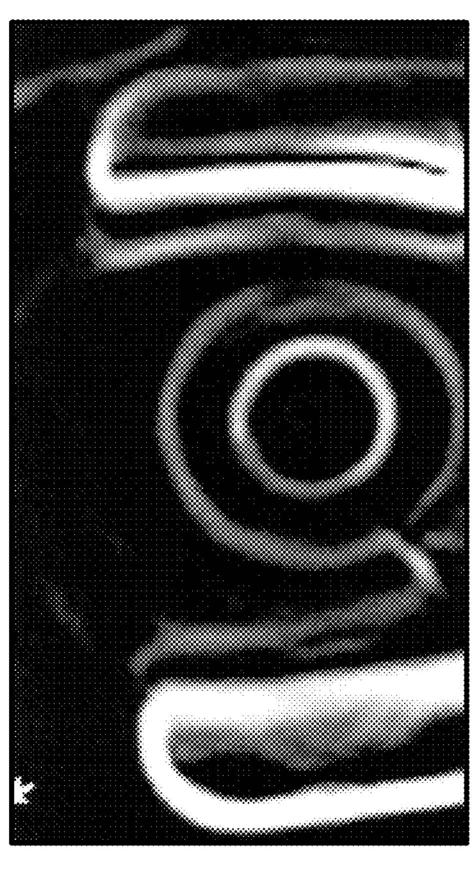

In one aspect, and as schematically shown in FIG. 7B, the features in a respective first image frame taken from the microscope video stream and analyzed and compared to a respective "downstream" second image frame taken from the microscope video stream, which is taken at a select time interval after the first image frame. It will be appreciated that the select time interval can be user selected, but preferably, the select time interval would be equivalent to the time interval required for the processor to identify the features in both the first and second image frame and to determine any movement of the eye based on the changes of the respective locations of the identified features from the first to the second image frame. In embodiments, it is contemplated that the selected time intervals can be between about every 15 to 70 milliseconds, preferably about between every 20 to 65 milliseconds, and more preferably between about every 28.5 to 50 milliseconds.

In embodiments, this tracking process can be iteratively done for each frame image in the microscope video stream. Optionally, the tracking process can be selected to be iteratively with a selected gap between the analyzed image frames. In this optional aspect and not meant to be limiting, using a selected gap could allow for every other frame of the microscope video steam to undergo the iterative tracking analysis.

In embodiments, it is preferred that the anchor frame is the same video frame image that is used in the registration process. In further embodiments, because the iris is already detected and fully described in the registration process, it may be desired to detect and describe the sclera region of the eye so that multiple appropriate landmarks or features in both the iris and the sclera can be used for tracking.

In operation, and again referring to FIG. 7B, the tracking process can be considered unreliable when the projection error between the tracked landmarks or features (T points) and the anchor landmarks or features (A points) is determined to be larger than a target threshold in pixels. This threshold can be less than 15 [px], preferably less than 10 [px], more preferred less than 5 [px], and most preferred being 3.5 [px] or less. In operation, it is preferred that, if the tracking process in determined to be unreliable, the guidance overlay will disappear from the surgeon's view. In this embodiment, it is contemplated that the tracking process would continue to operate and, once the tracking process in again determined to be reliable, the surgical guidance overlay will reappear in the surgeon's vision.

In exemplarily aspects, a description of the sclera region of the patient's eye aims to exclude as much non-sclera (and non-iris) as possible, while including reasonable amounts of sclera (and iris). This allows for the tracking methodology to identify enough valid landmarks or features to allow for accurate tracking of eye movement over the course of the surgical procedure.

In embodiments for detecting and describing the sclera region of the patient's eye, techniques including, but not limited to, de-interlacing, down-sampling, noise removal, edge detection and region growing are used.

In embodiments and referring to step 530 of FIG. 5B, various surgical steps that can be guided by the surgical guidance subsystem are identified. After the surgical procedure is accomplished, the surgeon can initiate a summary of the surgery in step 550 and can save the procedure video and details in a subsequent step 560.

In embodiments, exemplary GUI screens that can be provided by the surgical guidance subsystem 30 are illustrated in FIGS. 9A-9J.

Figure 9A:
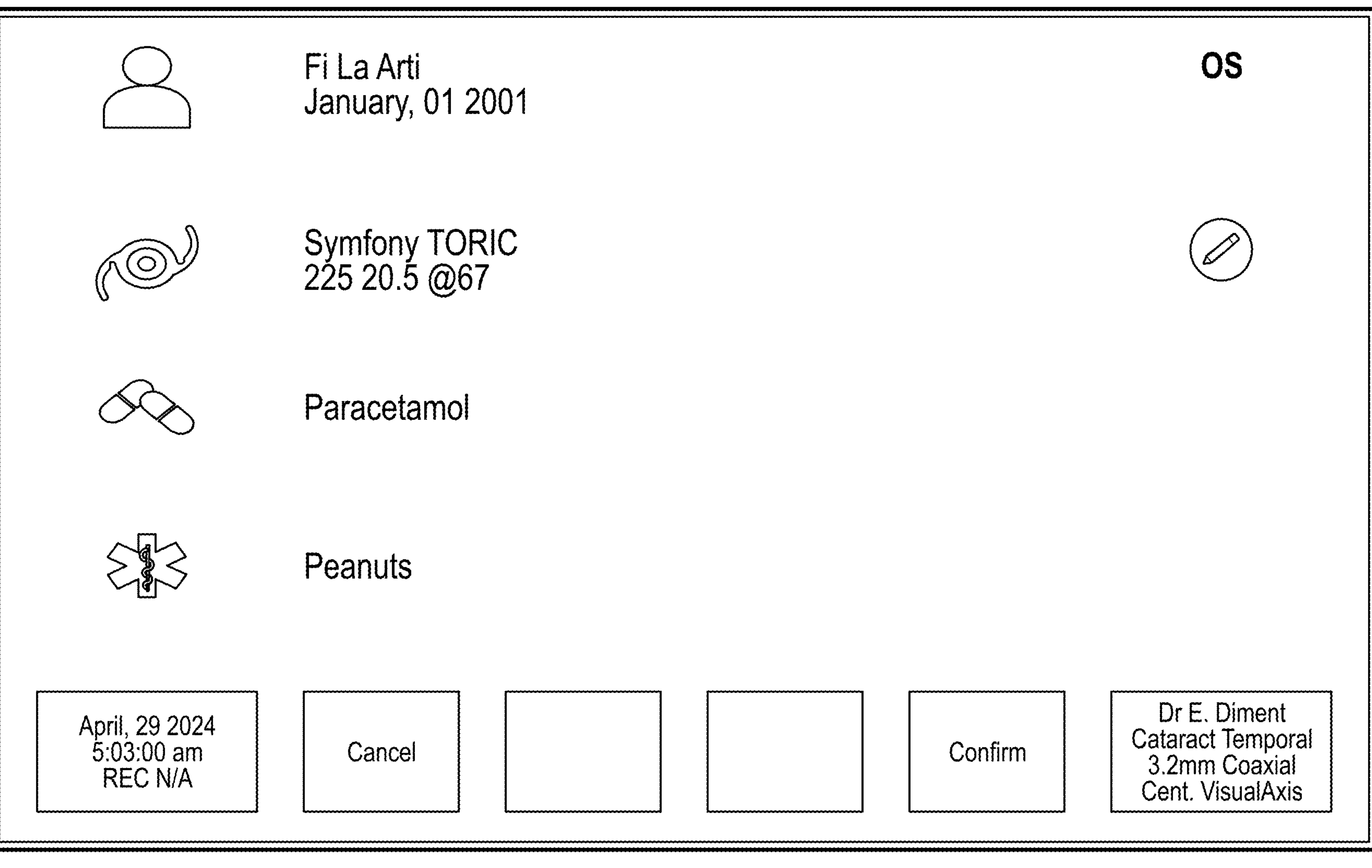
FIGS. 9A-9J illustrate exemplary GUI screens that can be provided by the surgical guidance subsystem.

In one aspect, FIG. 9A shows an exemplary image of a video output view or simply 'screen' of the surgical guidance system. This screen, which is displayed in a patient time-out state prior to initiation of the surgical guidance procedure, can display one or more of the following:

- Patient information, such as, for example, the patient's prefix, first name, last name, date of birth, patient age (displayed in an image box in the upper left corner);
- Time information, such as, for example, the date and time, and an indicator of whether recording of the surgical procedure is selected on or off (displayed in an image box in the bottom left corner);

Dynamic registration information, such as, for example, showing the status of the registration of the image of the eye provided by the planning subsystem to an image of the eye in near real-time as being either: INACTIVE/IN PROCESS/MODERATE/FAIL/SUCCESS and can include the automatic correction for the amount of cyclorotation (displayed in an image box in the top right corner);

Surgeon's information, such as, for example, the surgeon's name; the surgical profile selected in the planning subsystem, the incision location (e.g., either temporal or superior) and size in millimeters, the phacoemulsification technique (e.g., either Coax or Biman) selected in planning software; and basis of centration selected in the planning subsystem (e.g., either Center of Limbus or Visual Axis (displayed in an image box in the bottom right corner);

The patient photo (if available) and additional information to include, for example and without limitation, patient medication; previous eye surgery, additional patient pathology, patient allergies; patient family history; patient hobbies; patient's occupation; patient contact lenses data; additional notes, and the like (displayed in image box(es) in the top middle section); and Registration information can include, for example and without limitation, the Pre-Op Ant./TCA Astigmatism (e.g., the amount of cyl in +form @ axis in degrees that was generated or as selected in the planning subsystem), the Pred. Res. Astigmatism (e.g., the amount of cyl in +form @ axis in degrees that was generated or as selected in the planning subsystem), the IOL Model (e.g., the Name of model and the selected SE Power and Toric label as selected in the planning subsystem), and the IOL Axis Align in degrees as selected in the planning subsystem, (displayed in image box in the right middle section).

In embodiments, a time-out screen can include at least one action button. It is contemplated that the at least one action button can include a plurality of action buttons as exemplarily shown. In this non-limiting example, the plurality of action buttons, the action buttons can include four action buttons. In operation, it is contemplated that the respective action buttons can change with respect to function as the surgical guidance procedure moves from step to step. Further, the border of the respective action button can be configured to change color or shape to indicate whether or not the action button is active or not (i.e., for example and without limitation, the border of the action button can be displayed in a white color to indicate the button is active or the border can be displayed in a contrasting color or can be missing to indicate that the button is not active. Optionally, the border of an action button can be colored green or colored in another contrasting color to indicate a suggested course of action. For example; on the initial home page displayed, only two action buttons are being displayed in the field of four available action display button boxes in the bottom middle section—a cancel button, which, if selected, will revert the home screen to a case listing screen, and a confirm screen, which, if selected, confirms the patient case information, selected surgical plan, and initiates recording (if selected) and the registration decision guidance stage of the surgical guidance procedure.

Figure 9B:
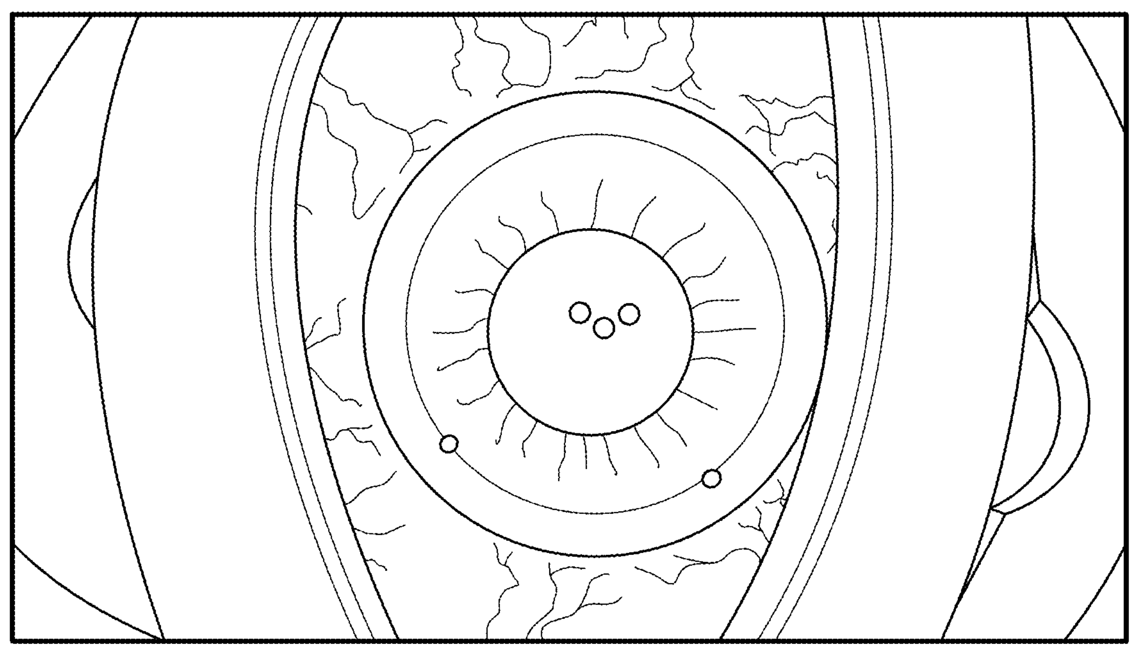

In embodiments, as shown in FIG. 9B, the dynamic registration information registration image box in the registration decision guidance stage screen displays that the registration system is INACTIVE and no cyclorotation information is provided in this stage (displayed in an image box in the top right corner). Regarding the action buttons, only two action buttons are being displayed in the field of four available action display button boxes in the bottom middle section—a REG. OFF button, which allows the surgeon to continue without registration or guidance functionalities (which provides for visualization and recording functionality only), and a REG. ON button, which allows the user to select the registration functionality.

Figure 9C:
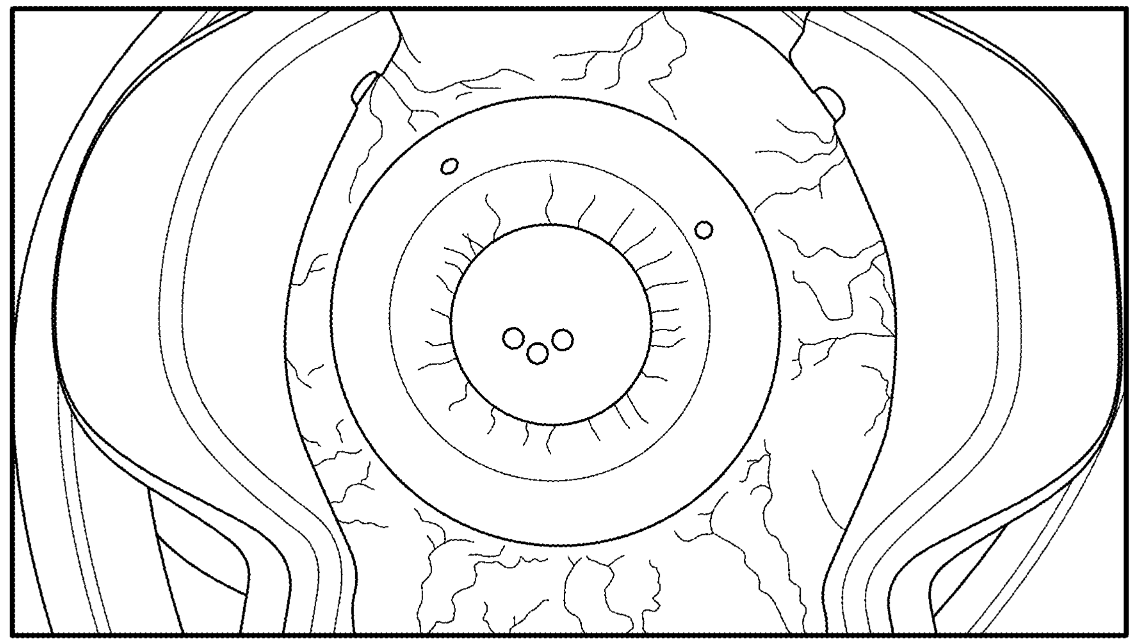

As shown in FIG. 9C, if the REG. OFF button is selected, the screen enters in a state where no dynamic guidance overlays are displayed. On this screen, the dynamic registration information box indicates that the registration system is INACTIVE and no cyclorotation information is provided. Registration information, to include the IOL model information and the selected SE power and Toric label (if available) can be displayed as well as the IOL axis align information in degrees can be provided if Toric was selected in the planning subsystem. On this registration off screen, only a subset of the action buttons can be available—e.g. a BACK button, which allows the surgeon to revert to the screen shown in FIG. 9B, a SAVE button, which allows a surgeon to finish and save the case but not mark it as complete and a SAVE & FINISH button, which also finishes the case and marks it as complete.

Figure 9D:
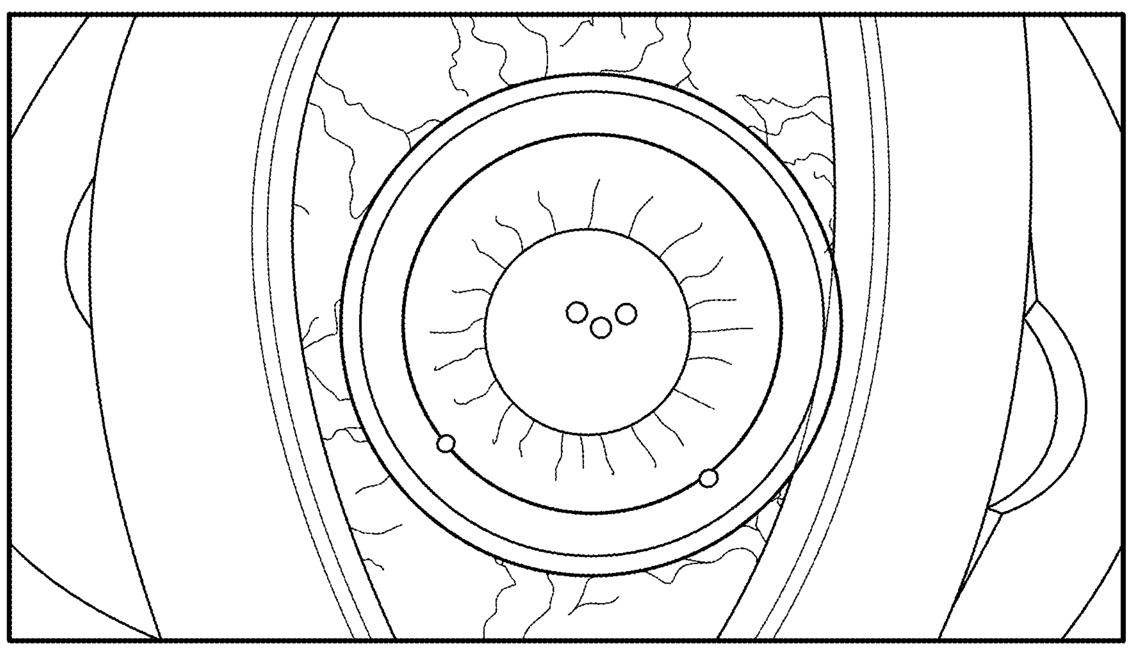

As shown in FIG. 9D, if the REG. ON button is selected, a registration alignment screen is displayed. On this screen, the dynamic registration information registration image box indicates that the registration system is IN PROCESS and no cyclorotation information is immediately provided. A pair of spaced circular rings are displayed that overlay the patient's eye and that define a circular band in which the outer edge of the iris of the patient's eye is defined. Thus, the circular band has a radial dimension that is large enough such that that outer edge of the iris of the patient's eye, which is generally non-uniform in radial length from the center of the eye, is bounded within the formed circular band. On this screen, two action buttons are displayed—a REG. OFF button, which allows the surgeon to deactivate the registration process, and a CAPTURE button, which allows the operator to capture a registration reference image from the video stream at the moment of button selection.

In operation and to affect the circular band creation, a semi-transparent Drape Navigation tool will appear in the center of the screen and the surgeon can adjust, as necessary, the zoom (Z-Axis) and move either the microscope or patient in such a manner that the limbus generally falls within the center (X/Y-Axes) of the formed circular band. Further, surgeons will be instructed to ensure clear focus and clarity of the sclera and iris upon the moment of image capture. Once optimal alignment and sharpness has been achieved, then an operator can select the CAPTURE button to acquire the image frame from the video stream. In further embodiments, instructions boxes can also be displayed on the screen for the surgeon—reminding the surgeon regarding the following actions: center the limbus of the eye within the circular band; ensure that the sclera and iris of the eye is in focus; ensure that no liquids or fluid build-up is present in the eye at moment of image acquisition; and ensure that focus is maintained during image acquisition.

After the CAPTURE button is selected and the registration reference image is captured, the registration announcement stage is initiated automatically. It is contemplated that the registration process will take less than 10 seconds, preferably less than 7 seconds, more preferably less than 5 seconds, still more preferably less than 3 seconds. In one preferred embodiment, the registration process will take less than 2 seconds. After the registration process is completed, a screen is displayed that corresponds to one of three different registration identifier options: MODERATE, which is indicative of registration within a desired level of accuracy at a confidence level of greater than about 50%; FAIL, which is indicative of an inability of the surgical guidance subsystem to successfully complete the registration process and achieve registration within a desired level of accuracy at a confidence level that is greater than about 50%; and SUCCESS, which is indicative of registration within a desired level of accuracy at a confidence level of greater than about 85%. In optional embodiments, the registration identifier MODERATE can preferably indicate registration within the desired level of degrees of accuracy having a confidence level of between about 50% to about 85%. In other embodiments, it is contemplated that the desired level of accuracy for registration can be between about 1 to about 4 degrees, preferably between about 1.5 to about 3 degrees, and more preferably about 2 degrees.

Figure 9E:
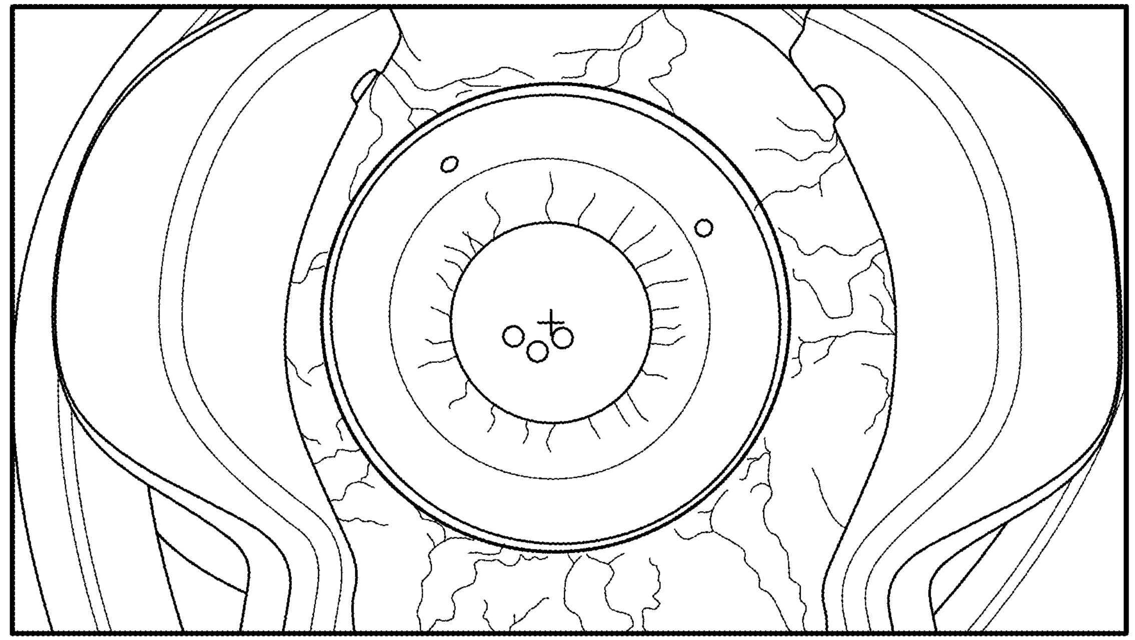

As exemplarily shown in FIG. 9E, in the MODERATE registration announcement state screen, the dynamic registration information registration image box indicates that registration system is in a MODERATE state and displays the number of degrees of cyclotorsion that is being automatically corrected by the surgical guidance subsystem.

On this screen, three action buttons are displayed—a GUIDE OFF button, which allows the surgeon to selectively toggle between the guide tool being in an active state or being placed in an inactive state, a RE-TAKE button, which allows the surgeon to retake and repeat the registration process, and an CONFIRM button, which allows the user to move to the next step in the process confirming the MODERATE (thus sub-optimal) registration.

In a further aspect shown in FIG. 9E, guidance tool information can be displayed to overlay the patient's eye. In various aspects, the guidance tool information that can be displayed on this screen can include one or more of: a green circle which can be fitted about the limbus of the patient's eye, a pair of dotted lines that indicate 0° and 180°, a centration cross which indicates Visual Axis or Angle Alpha location (which data is measured and supplied to the planning subsystem by the image processing subsystem and which can be selected as a portion of the surgical plan for use in the surgical guidance subsystem in the planning subsystem), Pre-Op Astigmatism (Ant./TCA data as measured and supplied to the planning subsystem by the image processing subsystem and which can be selected as a portion of the surgical plan for use in the surgical guidance subsystem in the planning subsystem). In operation, it is contemplated that the magnitude and axis of patient astigmatism will be indicated along a pre-op steep axis line. It is noteworthy that the magnitude and axis of patient astigmatism shown at this step is only informative during the registration announcement process.

Figure 9F:
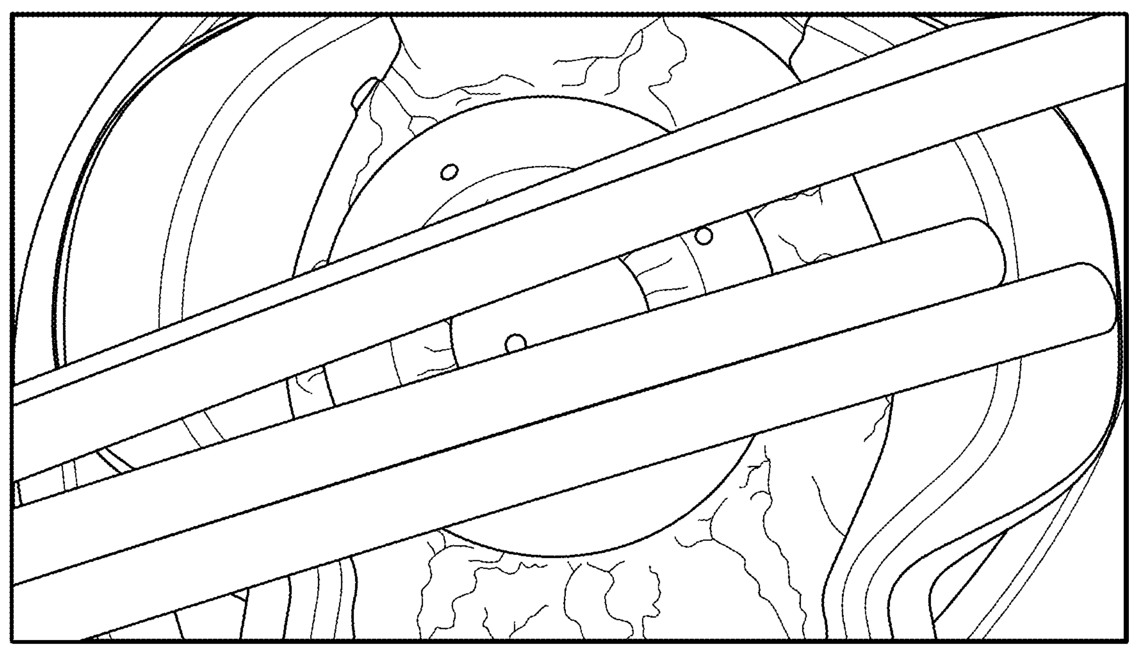

As exemplarily shown in FIG. 9F, in the FAIL registration announcement state screen, the dynamic registration information registration image box indicates that registration system is in a FAIL state and no dynamic guidance information is shown. In operation, the cause of the failed registration and the notification of the FAIL state, can be that at least a portion of the eye is obscured due to e.g. instruments, or the overall quality (focus, zoom) is found to be inadequate. On this screen, two action buttons are displayed—a REG. OFF button, which allows the surgeon to deactivate the registration process, for instance if the source of the fail cannot be eliminated, a RE-TAKE button, which allows the surgeon to retake and repeat the registration process. In a FAIL case there is no ACCEPT or CONFIRM button.

Figure 9G:
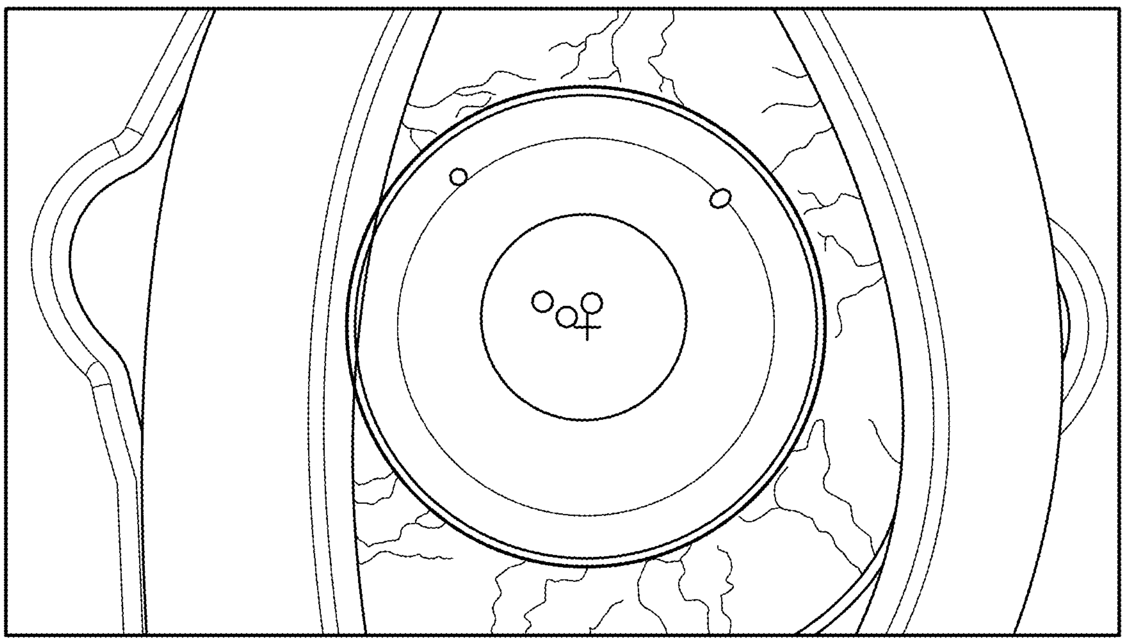

As exemplarily shown in FIG. 9G, in the SUCCESS registration announcement state screen, the dynamic registration information registration image box indicates that registration system is in a SUCCESS state and displays the number of degrees of cyclotorsion that is being automatically corrected by the surgical guidance subsystem. On this screen, three action buttons are displayed—a BACK button, which allows the surgeon to revert to the previous step, a GUIDE OFF button, which allows the surgeon to selectively toggle between the guide tool being in an active state or being placed in an inactive state, and an ACCEPT button, which allows the user to move to the next step in the process.

In a further aspect shown in FIG. 9G, guidance tool information can be displayed to overly the patient's eye. In various aspects, the guidance tool information that can be displayed on this screen can include one or more of: a green circle which can be fitted about the limbus of the patient's eye, a pair of dotted lines that indicate 0° and 180° of the pre-operative axis, a centration cross which indicates Visual Axis or Angle Alpha location (which data is measured and supplied to the planning subsystem by the image processing subsystem and which can be selected as a portion of the surgical plan for use in the surgical guidance subsystem in the planning subsystem), Pre-Op Astigmatism (Ant./TCA data as measured and supplied to the planning subsystem by the image processing subsystem and which can be selected as a portion of the surgical plan for use in the surgical guidance subsystem in the planning subsystem). In operation, it is contemplated that the magnitude and axis of patient astigmatism will be indicated along a pre-op steep axis line. It is noteworthy that the magnitude and axis of patient astigmatism shown at this step is only informative during the registration announcement process.

In a further aspect, information boxes can also be displayed on the screen for the surgeon—identifying: Pre-Op Astigmatism/TCA Astigmatism (Ant./TCA data as measured and supplied to the planning subsystem by the image processing subsystem and which is selected as a portion of the surgical plan for use in the surgical guidance subsystem in the planning subsystem); Pred. Res. Astigmatism (as determined by the planning subsystem); IOL Model information (as selected in the planning subsystem); selected SE Power (as selected in the planning subsystem); a Toric label (if a Toric IOL was selected in planning subsystem) and the IOL Axis Alignment in degrees (if a Toric IOL was selected in Planning subsystem).

Figure 9H:
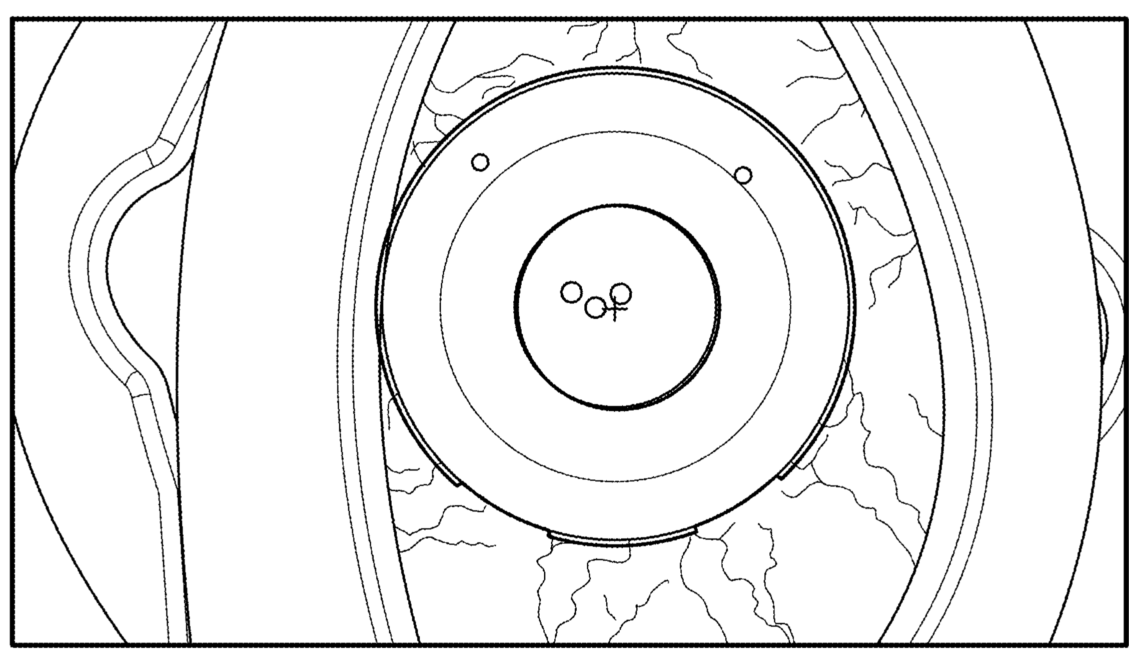

After the ACCEPT button on the in the SUCCESS registration announcement state screen is selected, and "non-Toric" was selected in the planning subsystem for the surgical plan, the combined surgical guidance tool screen (for NON TORIC IOL), as exemplarily shown in FIG. 9H, is displayed. As exemplarily shown in FIG. 9H, the dynamic registration information registration image box indicates that registration system is in a SUCCESS state and displays the number of degrees of cyclotorsion that is being automatically corrected by the surgical guidance subsystem. On this screen, four action buttons are displayed—a GUIDE OFF button, which allows the surgeon to selectively toggle between the guide tool being in an active state or being placed in an inactive state, a REFIT button which allows the surgeon to actualize the information used by the tracker, a SNAPSHOT button to trigger the acquisition of a snapshot for later use, and DONE, which allows the user to move to the next step in the process.

In embodiments and as exemplarily shown in FIG. 9H, guidance tool information that can be displayed on this combined surgical overlay screen can include one or more of: a first green circle which can be fitted about the limbus of the patient's eye, a centration cross which indicates Visual Axis or Angle Alpha location (which data is measured and supplied to the planning subsystem by the image processing subsystem and which can be selected as a portion of the surgical plan for use in the surgical guidance subsystem in the planning subsystem); a second green circle that has a smaller diameter than the first green circle, the second green circle being positioned within the first green circle (the diameter size and the centration location of the second green circle being measured and supplied by the image processing subsystem to the planning subsystem and which can be selected as a portion of the surgical plan for use in the surgical guidance subsystem in the planning subsystem) for instance to guide a capsulotomy; a main incision opening location, which is at the same location as the previously noted main incision location indicator, defining a notch extending inwardly from the first green circle toward the inside of the limbus block; a paracentesis incision opening location, which is at the same location as the previously noted paracentesis incision location indicator, defining a small notch extending inwardly from the first green circle toward the inside of the limbus block; and a pair of dotted lines that indicate 0° and 180° of the pre-operative axis, as well pair of visually distinct dotted/dashed lines that indicate the location of the steep axis of astigmatism.

Figure 9I:
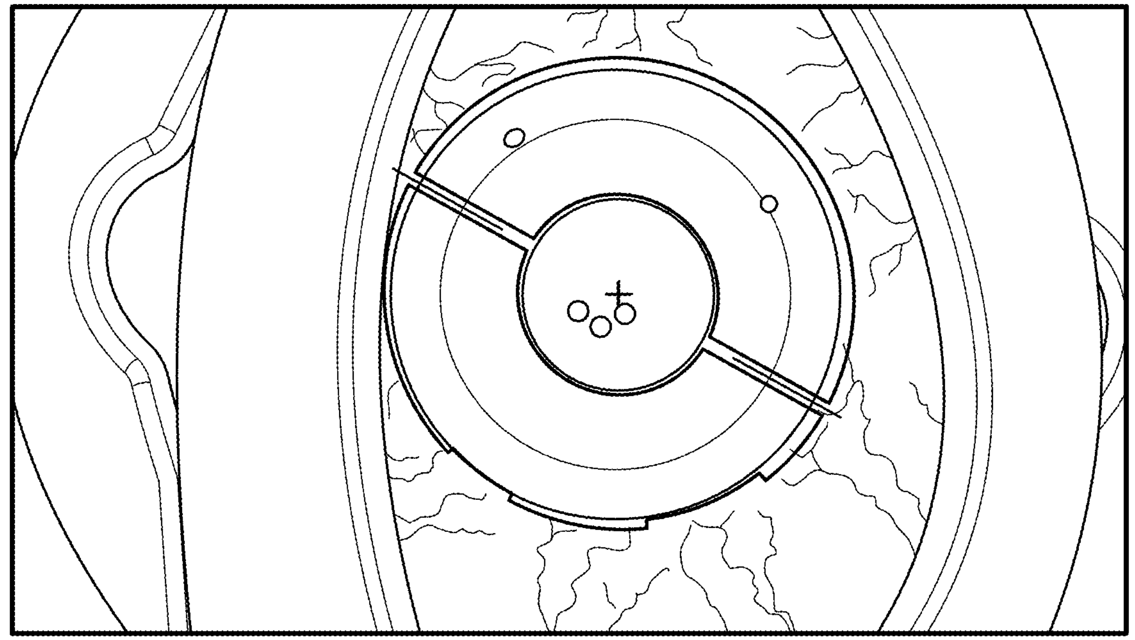

After the ACCEPT button on the in the SUCCESS registration announcement state screen is selected, and "Toric" was selected in the planning subsystem for the surgical plan, the combined surgical overlay screen (for TORIC IOL), as exemplarily shown in FIG. 9I, is displayed. As exemplarily shown, in this combined overlay screen, the dynamic registration information registration image box indicates that registration system is in a SUCCESS state and displays the number of degrees of cyclotorsion that is being automatically corrected by the surgical guidance subsystem. In a further aspect, the dynamic registration information registration image box can also show TORIC IOL information such as, for example and without limitation, IOL Model information (as selected in the planning subsystem); selected SE Power (as selected in the planning subsystem); a Toric label and the IOL Axis Alignment in degrees.

On this combined surgical overlay screen (for TORIC IOL), four action buttons are displayed—a GUIDE OFF button, which allows the surgeon to selectively toggle between the guide tool being in an active state or being placed in an inactive state, a SNAPSHOT button, which allows the user to take images from the video as desired (it is contemplated that only the latest image taken is saved and can be included in a Surgery Summary Report), a GUIDE OFF button, which allows the surgeon to selectively toggle between the guide tool being in an active state or being placed in an inactive state, and a DONE button, which allows the user to move to the next step in the process.

In embodiments and as exemplarily shown in FIG. 9I, guidance tool information that can be displayed on this centration and alignment identification screen (for TORIC IOL) can include one or more of: a pair of opposing semi-circular bands having an outer green circular portion which can be fitted about the limbus of the patient's eye and an inner green circular portion that is fitted inwardly about the limbus of the patient's eye, the respective opposing ends of the pair of opposing semi-circular bands defining a pair of channels that are oriented 180 degrees apart and that extend and are spaced from a co-axial axis of the pair of channels, a pair of opposed, co-axial green lines that extend from outside of the outer radii of the pair of opposing semi-circular bands along the co-axial axis of the pair of channels to a position between the radii of the outer green circle and the radii of the inner green circle (as exemplified, the co-axial axis is positioned to identify and display the steep axis), a centration cross which indicates Visual Axis or Angle Alpha location (which data is measured and supplied to the planning subsystem by the image processing subsystem and which can be selected as a portion of the surgical plan for use in the surgical guidance subsystem in the planning subsystem), a main incision opening location, which is at the same location as the previously noted main incision location indicator, defining a notch extending inwardly from the outer green circular portion toward the inside of the limbus block; a paracentesis incision opening location, which is at the same location as the previously noted paracentesis incision location indicator, defining a small notch extending inwardly from the outer green circular portion toward the inside of the limbus block; a pair of dotted lines that indicate 0° and 180°, and a label with the steep axis direction (as determined in the planning subsystem) and Toric label, which can be positioned proximate a distal end of one of the pair of opposed, co-axial green lines.

Figure 9J:
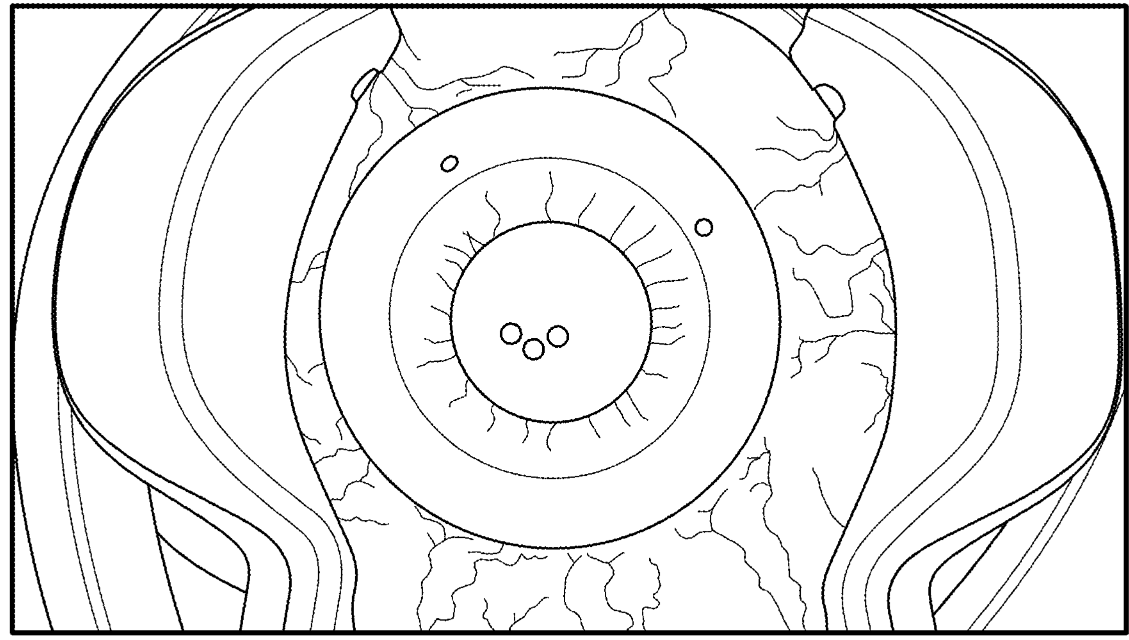

In the final stage of the process, as shown in FIG. 9J, the workflow finalizing screen (for TORIC or NON TORIC IOL), as exemplarily shown in FIG. 9J, the dynamic registration information registration image box indicates that registration system is in a SUCCESS state and displays the number of degrees of cyclotorsion that is being automatically corrected by the surgical guidance subsystem. In a further aspect, the dynamic registration information registration image box can also show TORIC IOL information such as, for example and without limitation, IOL Model information (as selected in the planning subsystem); selected SE Power (as selected in the planning subsystem); and a Toric label. No IOL Axis Alignment information is provided this screen as non-Toric was selected in the surgical plan developed in the planning subsystem.

On this screen, the operator has time to administer any desired medicants, such as, for example and not meant to be limiting, eye drops, and to perform a final inspection. Three action buttons are displayed—a BACK button, which allows the surgeon to revert to a previous step in the surgical guidance process, a SAVE button, which allows the surgeon to indicate they have completed the procedure but do not want to mark the case as completed, and a SAVE & FINISH button, which allows the surgeon to indicate that they have completed the procedure, both terminates the procedure time clock and allows the surgeon to select a new patient case.

Figure 10:
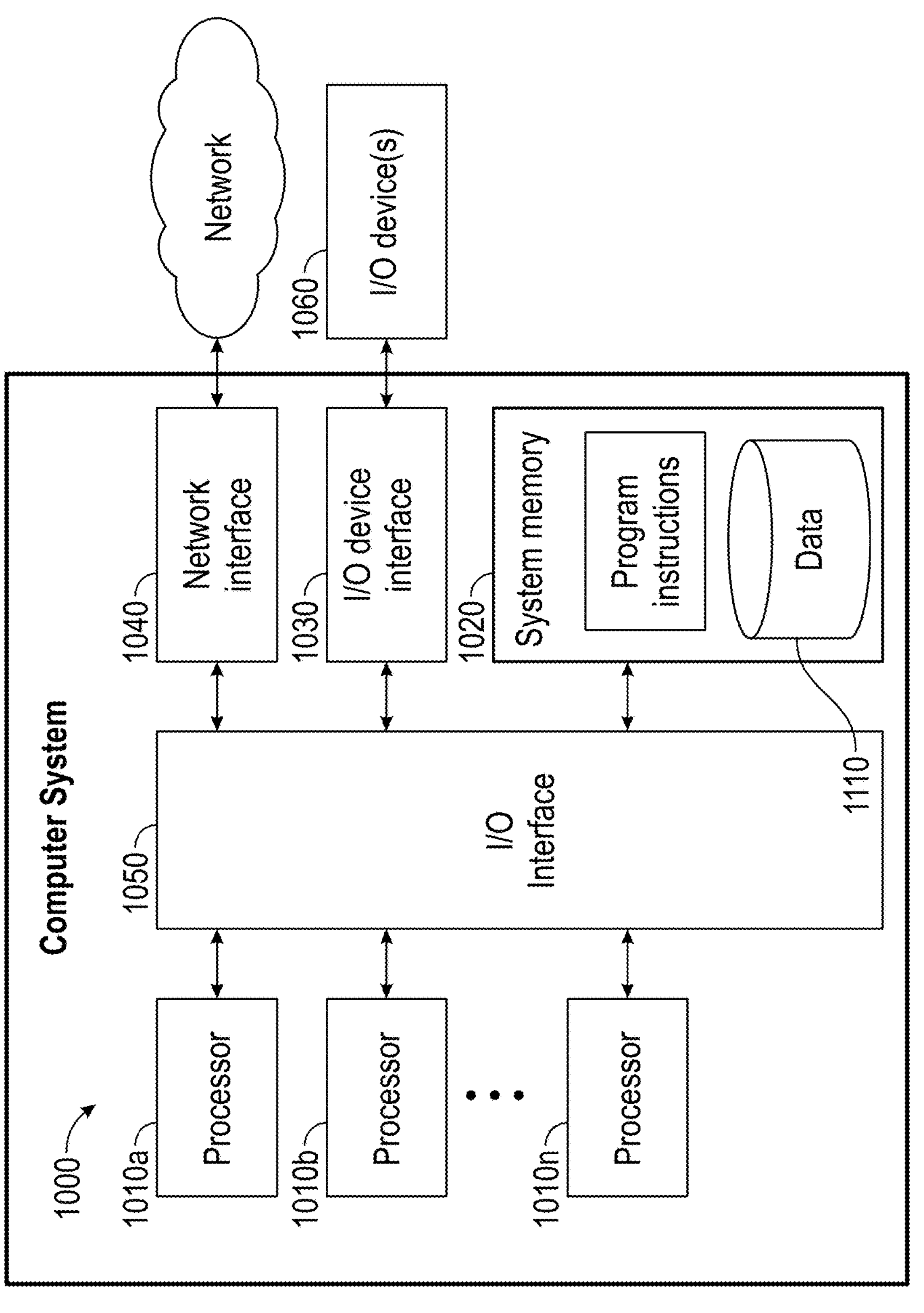
FIG. 10 is a schematic diagram that illustrates an exemplary computer system.

Exemplary Computer System(s) for the Image Processing Subsystem, the Planning Subsystem, and the Surgical Guidance Subsystem FIG. 10 is a diagram that illustrates an exemplary computer system 1000 in accordance with one or more embodiments of the present technique. Various portions of systems and methods described herein, may include or be executed on one or more computer systems similar to system 1000. Further, methods/processes/applications or modules/subsystems described herein may be executed by one or more processing systems similar to that of the exemplary computer system 1000.

Exemplary computer system 1000 can include one or more processors (e.g., processors 1010*a*-1010*n*) coupled to a system memory 1020, an input/output I/O device interface 1030 and, optionally, a network interface 1040 via an input/output (I/O) interface 1050. A processor can include a single processor device and/or a plurality of processor devices (e.g., distributed processors). A processor can be any suitable processor capable of executing/performing instructions. A processor can include a central processing unit (CPU) that carries out program instructions to perform the basic arithmetical, logical, and input/output operations of computer system 1000. A processor may include code (e.g., processor firmware, a protocol stack, a database management system, an operating system, or a combination thereof) that creates an execution environment for program instructions. A processor can include a programmable processor. A processor can include general and/or special purpose microprocessors. A processor can receive instructions and data from a memory (e.g., system memory 1020). Computer system 1000 may be a uni-processor system including one processor (e.g., processor 1010*a*), or a multi-processor system including any number of suitable processors (e.g., 1010*a*-1010*n*). Multiple processors can be employed to provide for parallel and/or sequential execution of one or more portions of the techniques described herein. Processes and logic flows described herein can be performed by one or more programmable processors executing one or more computer programs to perform functions by operating on input data and generating corresponding output. Processes and logic flows described herein can be performed by, and apparatus can also be implemented as, special purpose logic circuitry, e.g., an FPGA (field programmable gate array) or an ASIC (application specific integrated circuit). Computer system 1000 can include a computer system employing a plurality of computer systems (e.g., distributed computer systems) to implement various processing functions.

I/O device interface 1030 can provide an interface for connection of one or more I/O devices 1060 to computer system 1000. I/O devices can include any device that provides for receiving input (e.g., from a user and/or system) and/or providing output (e.g., to a user and/or system). I/O devices 1060 can include, for example, graphical user interface displays (e.g., a cathode ray tube (CRT), a liquid crystal display (LCD) monitor, and the like), pointing devices (e.g., a computer mouse, a trackball, and the like), keyboards, keypads, touchpads, scanning devices, voice recognition devices, gesture recognition devices, printers, audio speakers, microphones, cameras, and/or the like. I/O devices 1060 can be connected to computer system 1000 through a wired or wireless connection. I/O devices 1060 can be connected to computer system 1000 from a remote location. I/O devices 1060 located on remote computer system, for example, can be connected to computer system 1000 via a network and network interface 1040.

Network interface 1040 may include a network adapter that provides for connection of computer system 1000 to a network. Network interface 1040 can facilitate data exchange between computer system 1000 and other devices/modules/subsystems connected to the network. Network interface 1040 can support wired or wireless communication. The network can include an electronic communication network, such as the Internet, a local area network (LAN), a wide area (WAN), a cellular communications network or the like.

System memory 1020 can be configured to store program instructions 1100 and/or data 1040. Program instructions 1100 can be executable by a processor (e.g., one or more of processors 1010*a*-1010*n*) to implement one or more embodiments of the present technique. Instructions 1100 can include modules of computer program instructions for implementing one or more techniques described herein with regard to various processing steps for the respective image processing, planning, and surgical guidance subsystems. Program instructions can include a computer program (also known as a program, software, software application, script, or code). A computer program can be written in any form of programming language, including compiled or interpreted languages, or declarative/procedural languages. A computer program can include a unit suitable for use in a computing environment, including as a stand-alone program, a module, a component, a subroutine. A computer program can or cannot correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one or more computer processors located locally at one site or distributed across multiple remote sites and interconnected by a communication network.

System memory 1020 can include a tangible program carrier and/or a non-transitory computer readable storage medium having program instructions stored thereon. A tangible program carrier can include a propagated signal and/or a non-transitory computer readable storage medium. A propagated signal can include an artificially generated signal (e.g., a machine generated electrical, optical, or electromagnetic signal) having encoded information embedded therein. The propagated signal can be transmitted by a suitable transmitter device to and/or received by a suitable receiver device. A non-transitory computer readable storage medium can include, without limitation, a machine readable storage device, a machine readable storage substrate, a memory device, or any combination thereof. Non-transitory computer readable storage medium can include, without limitation, non-volatile memory (e.g., flash memory, ROM, PROM, EPROM, EEPROM memory), volatile memory (e.g., random access memory (RAM), static random access memory (SRAM), synchronous dynamic RAM (SDRAM)), bulk storage memory (e.g., CD-ROM and/or DVD-ROM, hard-drives), or the like. System memory 1020 can include a non-transitory computer readable storage medium that can have program instructions stored thereon that are executable by a computer processor (e.g., one or more of processors 1010*a*-1010*n*) to cause the subject matter and the functional operations described herein. A memory (e.g., system memory 1020) can include a single memory device and/or a plurality of memory devices (e.g., distributed memory devices).

I/O interface 1050 can be configured to coordinate I/O traffic between processors 1010*a*-1010*n*, system memory 1020, network interface 1040, I/O devices 1060 and/or other peripheral devices. I/O interface 1050 can perform protocol, timing or other data transformations to convert data signals from one component (e.g., system memory 1020) into a format suitable for use by another component (e.g., processors 1010*a*-1010*n*). I/O interface 1050 can include support for devices attached through various types of peripheral buses, such as a variant of the Peripheral Component Interconnect (PCI) bus standard or the Universal Serial Bus (USB) standard.

Embodiments of the techniques described herein can be implemented using a single instance of computer system 1000, or multiple computer systems 1000 configured to host different portions or instances of embodiments. Multiple computer systems 1000 can provide for parallel or sequential processing/execution of one or more portions of the techniques described herein.

Those skilled in the art will appreciate that computer system 1000 is merely illustrative and is not intended to limit the scope of the techniques described herein. Computer system 1000 can include any combination of devices and/or software that can perform or otherwise provide for the performance of the techniques described herein. Computer system 1000 can also be connected to other devices that are not illustrated or may operate as a stand-alone system. In addition, the functionality provided by the illustrated components can in some embodiments be combined in fewer components or distributed in additional components. Similarly, in some embodiments, the functionality of some of the illustrated components may not be provided and/or other additional functionality can be available.

Those skilled in the art will also appreciate that, while various items are illustrated as being stored in memory or on storage while being used, these items or portions of them can be transferred between memory and other storage devices for purposes of memory management and data integrity. Alternatively, in other embodiments some or all of the software components can execute in memory on another device and communicate with the illustrated computer system via inter-computer communication. Some or all of the system components or data structures can also be stored (e.g., as instructions or structured data) on a computer-accessible medium or a portable article to be read by an appropriate drive, various examples of which are described above. In some embodiments, instructions stored on a computer-accessible medium separate from computer system 1000 can be transmitted to computer system 1000 via transmission media or signals such as electrical, electromagnetic, or digital signals, conveyed via a communication medium such as a network and/or a wireless link. Various embodiments can further include receiving, sending or storing instructions and/or data implemented in accordance with the foregoing description upon a computer-accessible medium. Accordingly, the present invention may be practiced with other computer system configurations.

The foregoing has described various embodiments of a surgical guidance systems and methods of operation thereof; and, in particular, to surgical guidance systems utilizing novel registration and tracking modalities. The disclosed systems and methods are provided to illustrate the essential and optional features and functions, and those skilled in the art may conceive of alternatives or modifications that do not depart from the principles of the invention as encompassed by the appended claims, and that such alternatives or modifications may be functionally equivalent.

What is claimed is:

1. An ophthalmologic surgical system operatively coupled to a surgical microscope for use in a guided surgical procedure on an eye of a patient, comprising:

a planning subsystem comprising a processor programed to produce a surgical plan based on inputs that include: a preoperative image of the eye, preoperative topographic eye data, surgical profile information and surgical plan data; and a surgical guidance subsystem comprising a processor programed to provide operations including:

registering a real-time video image of the patient's eye as displayed to the surgeon via the surgical microscope to an image of the eye of the patient generated by the planning subsystem;

providing surgical guidance imaging in a visual overlay throughout the surgical procedure in accord with the surgical plan;

continually updating the visual display at a rate sufficient to maintain accurate alignment of the visual display relative to the position of the eye;

continually tracking of a plurality of identified landmarks on the eye of the patient after eye registration to ensure accurate registration of the provided surgical guidance imaging relative to the eye of the patient irrespective to movement of the patient's eye throughout the surgical procedure;

comparing landmarks in a respective first image frame taken from the video stream generated by the surgical microscope to a respective downstream second image frame taken from the video stream generated by the surgical microscope, which is taken at a select time interval after the first image frame;

determining the error threshold between the tracked landmarks and the landmarks in an anchor video frame that was used when registering the real-time video image of the patient's eye, wherein the error threshold is exceeded when the error between the tracked landmarks and the anchor landmarks is determined to be larger than a target threshold; and terminating surgical guidance imaging in the visual overlay until the error threshold is less than the target threshold.

2. The ophthalmologic surgical system of claim 1, wherein the processor of the planning system is further programmed to verify desired eye orientation and planned surgical incisions prior to initiation of the guided surgical procedure.

3. The ophthalmologic surgical system of claim 1, wherein the surgical profile information includes one or more of: a desired sitting position for the operating physician; a desired Phaco technique; a centration preference; a desired size of the clear corneal incision; a desired paracentesis size; a desired angle of the center of the paracentesis in degrees relative to the 0-axis; a desired incision correction for cyclorotation; a surgical induced astigmatism; a desired capsulotomy diameter; and/or a desired overlay color scheme for the guidance module.

4. The ophthalmologic surgical system of claim 3, wherein the surgical profile information includes one or more of: the IOL manufacturer and model name; the spherical equivalent power of the IOL in the IOL plane; the cylindrical power of the IOL in the IOL plane; the cylindrical power of the IOL in the corneal plane; the angle of IOL axis relative to relative to the 0-axis; the predicted residual astigmatism, the angle of the predicted residual astigmatism; the keratometric steep power; the keratometric steep axis; and/or the keratometric flat power.

5. The ophthalmologic surgical system of claim 1, wherein the surgical plan data includes selectable surgical incision positions includes one or more of: a capsulotomy incision, a lens fragmentation incision, a cataract incision, and/or an arcuate incisions.

6. The ophthalmologic surgical system of claim 1, wherein registration of the real-time video image of the eye of the patient as displayed to the surgeon via the surgical microscope to an image of the eye of the patient generated by the planning subsystem provides for the correct orientation of the visual overlay that is superimposed over the view of the eye of the patient as shown in a video stream generated by the surgical microscope.

7. The ophthalmologic surgical system of claim 1, wherein the overlays are updated between about every 15 to 70 milliseconds.

8. The ophthalmologic surgical system of claim 1, wherein the rate that the overlays are updated is between about every 28.5 to 50 milliseconds.

9. The ophthalmologic surgical system of claim 1, wherein the plurality of identified landmarks are dispersed over the patient's eye.

10. The ophthalmologic surgical system of claim 9, wherein number of the plurality of identified landmarks is at least 5.

11. The ophthalmologic surgical system of claim 9, wherein number of the plurality of identified landmarks is between 5 to 100.

12. The ophthalmologic surgical system of claim 1, wherein the select time interval is the time required for the surgical guidance subsystem processor to identify the landmarks in both the first and second image frame and to determine any movement of the eye based on the changes of the respective locations of the identified landmarks from the first to the second image frame.

13. The ophthalmologic surgical system of claim 1, wherein the landmarks are identified in the iris region of the eye of the patient.

14. The ophthalmologic surgical system of claim 13, wherein the landmarks are identified in the sclera region of the eye of the patient.

15. The ophthalmologic surgical system of claim 1, wherein the error threshold is measured in pixels, and wherein the error threshold is less than about 15 pixels.

16. The ophthalmologic surgical system of claim 1, further comprising an image processing subsystem comprising a processor programmed to produce the preoperative image of the eye and the preoperative topographic data.

17. The ophthalmologic surgical system of claim 1, wherein the preoperative image of the eye is a color image of the eye.

18. The ophthalmologic surgical system of claim 1, wherein the preoperative topographic data includes one or more of: sagittal/Axial map data; anterior keratometric power data for steep axis; anterior axis value data for steep axis; posterior keratometric power data for steep axis; posterior axis value data for steep axis; Total Corneal Astigmatism (TCA) keratometric power data for steep axis; TCA axis value data for steep axis; anterior keratometric power data for flat axis; anterior axis value data for flat axis in degrees; anterior keratometric power data for flat axis in Diopter; posterior axis value data for flat axis; TCA keratometric power data for flat axis, and/or TCA axis value data for flat axis.

19. The ophthalmologic surgical system of claim 1, wherein the preoperative topographic data further incudes one or more of: limbus description data; pupil description data; the x, y coordinates of the visual axis; a distance from the center of the limbus to the visual axis, an angle from the center of the limbus to the visual axis, a distance from the center of the mesopic pupil to the visual axis, an angle from the center of the mesopic pupil to the visual axis; a distance from the center of the photopic pupil to the visual axis, and/or an angle from the center of the photopic pupil to the visual axis.

20. An ophthalmologic surgical system operatively coupled to a surgical microscope for use in a guided surgical procedure on an eye of a patient, comprising:

a surgical guidance subsystem comprising a processor programed to provide operations including:

registering a real-time video image of the patient's eye as displayed to the surgeon via the surgical microscope to an image of the eye of the patient;

providing surgical guidance imaging in a visual overlay throughout the surgical procedure in accord with a surgical plan;

continually tracking of a plurality of identified landmarks on the eye of the patient after eye registration to ensure accurate registration of the provided surgical guidance imaging relative to the eye of the patient irrespective to movement of the patient's eye throughout the surgical procedure;

comparing landmarks in a respective first image frame taken from the video stream generated by the surgical microscope to the landmarks in a respective downstream second image frame taken from the video stream generated by the surgical microscope, which is taken at a select time interval after the first image frame;

determining an error threshold between the tracked landmarks and the landmarks in an anchor video frame that was used when registering the real-time video image of the patient's eye, wherein the error threshold is exceeded when the error between the tracked landmarks and the anchor landmarks is determined to be larger than a target threshold; and terminating surgical guidance imaging in the visual overlay until the error threshold is less than the target threshold.

21. The ophthalmologic surgical system of claim 20, further comprising a planning subsystem comprising a processor programed to produce the surgical plan based on inputs that include: a preoperative image of the eye, preoperative topographic eye data, surgical profile information and surgical plan data.

22. The ophthalmologic surgical system of claim 21, further comprising an image processing subsystem comprising a processor programmed to produce the preoperative image of the eye and the preoperative topographic data.

23. The ophthalmologic surgical system of claim 21, wherein registration of the real-time video image of the patient's eye as displayed to the surgeon via the surgical microscope to an image of the eye of the patient generated by the planning subsystem provides for the correct orientation of the visual overlay that is superimposed over the view of the eye of the patient as shown in a video stream generated by the surgical microscope.

24. The ophthalmologic surgical system of claim 20, wherein the surgical guidance subsystem processor is further programed for continually updating the visual display at a rate sufficient to maintain accurate alignment of the visual display relative to the position of the eye, which rate allows the surgical guidance subsystem to effectively compensate for rapid eye movements.

25. The ophthalmologic surgical system of claim 24, wherein the rate that the overlays are updated is between about every 15 to 70 milliseconds.

26. The ophthalmologic surgical system of claim 20, wherein the plurality of identified landmarks are dispersed over the patient's eye.

27. The ophthalmologic surgical system of claim 26, wherein number of the plurality of identified landmarks is between 5 to 100.

28. The ophthalmologic surgical system of claim 20, wherein the select time interval is the time required for the surgical guidance subsystem processor to identify the landmarks in both the first and second image frame and to determine any movement of the eye based on the changes of the respective locations of the identified landmarks from the first to the second image frame.

29. The ophthalmologic surgical system of claim 20 wherein the error threshold is measured in pixels, and wherein the error threshold is less than about 15 pixels.

30. An ophthalmologic surgical system operatively coupled to a surgical microscope for use in a guided surgical procedure on an eye of a patient, comprising:

a surgical guidance subsystem comprising a processor programed to provide operations including:

registering a real-time video image of the patient's eye as displayed to the surgeon via the surgical microscope to an image of the eye of the patient;

providing a surgical guidance imaging in a visual overlay throughout the surgical procedure in accord with a surgical plan;

continually tracking of a plurality of identified landmarks on the eye of the patient after eye registration to ensure accurate registration of the provided surgical guidance imaging relative to the eye of the patient irrespective to movement of the patient's eye throughout the surgical procedure;

comparing landmarks in a respective first image frame taken from the video stream generated by the surgical microscope to the landmarks in a respective downstream second image frame taken from the video stream generated by the surgical microscope, which is taken at a select time interval after the first image frame;

determining an error threshold between the tracked landmarks and the landmarks in an anchor video frame that was used when registering the real-time video image of the patient's eye; and terminating the surgical guidance imaging in the visual overlay until the error threshold is less than the target threshold.

31. The ophthalmologic surgical system of claim 30, wherein the surgical guidance subsystem processor is further programed for continually updating the visual display at a rate sufficient to maintain accurate alignment of the visual display relative to the position of the eye, which rate allows the surgical guidance subsystem to effectively compensate for rapid eye movements.

32. The ophthalmologic surgical system of claim 30, wherein the select time interval is the time required for the surgical guidance subsystem processor to identify the landmarks in both the first and second image frame and to determine any movement of the eye based on the changes of the respective locations of the identified landmarks from the first to the second image frame.

33. The ophthalmologic surgical system of claim 30, wherein the error threshold is exceeded when the error between the tracked landmarks and the anchor landmarks is determined to be larger than a target threshold.

34. The ophthalmologic surgical system of claim 33, wherein the error threshold is measured in pixels, and wherein the error threshold is less than about 15 pixels.

35. The ophthalmologic surgical system of claim 34, wherein the error threshold is less than about 5 pixels.

* * * * *